United States Patent
Zhan et al.

(10) Patent No.: US 11,473,070 B2
(45) Date of Patent: Oct. 18, 2022

(54) INCREASED POLYPEPTIDE PRODUCTION YIELDS OF BUTYRYLCHOLINESTERASE POLYPEPTIDES FOR THERAPEUTIC USE

(71) Applicant: University of Kentucky Research Foundation, Lexington, KY (US)

(72) Inventors: Chang-Guo Zhan, Lexington, KY (US); Fang Zheng, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 86 days.

(21) Appl. No.: 17/129,736

(22) Filed: Dec. 21, 2020

(65) Prior Publication Data

US 2021/0189359 A1 Jun. 24, 2021

Related U.S. Application Data

(60) Provisional application No. 62/950,765, filed on Dec. 19, 2019.

(51) Int. Cl.
*C12N 9/18* (2006.01)

(52) U.S. Cl.
CPC ........ *C12N 9/18* (2013.01); *C12Y 301/01008* (2013.01); *C07K 2319/30* (2013.01)

(58) Field of Classification Search
None
See application file for complete search history.

(56) References Cited

U.S. PATENT DOCUMENTS

2019/0255155 A1* 8/2019 Perlroth .................. C07K 7/08

OTHER PUBLICATIONS

Cerasoli, et ao., In vitro and in vivo characterization of recombinant human butyrylcholinesterase (Protexia™) as a potential nerve agent bioscavenger, Chemico-biological interactions, 157 (2005) 362-365.
Ashani, et al., Butyrylcholinesterase and acetylcholinesterase prophylaxis against soman poisoning in mice, Biochem Pharmacol, 41 (1991) 37-41.
Brazzolotto, et al., Human butyrylcholinesterase produced in insect cells: huprine-based affinity purification and crystal structure, FEBS Journal, 279 (2012) 2905-2916.
Geyer, et al., Transgenic plants as a source for the bioscavenging enzyme, human butyrylcholinesterase, Plant biotechnology journal, 8 (2010) 873-886.
Huang, et al., Recombinant human butyrylcholinesterase from milk of transgenic animals to protect against organophosphate poisoning, Proc Natl Acad Sci U S A, 104 (2007) 13603-13608.
Nachon, et al., Engineering of a monomeric and low-glycosylated form of human butyrylcholinesterase, Eur. J. Biochem. 269, 630-637 (2002).

* cited by examiner

*Primary Examiner* — Suzanne M Noakes
*Assistant Examiner* — Jae W Lee
(74) *Attorney, Agent, or Firm* — Stites & Harbison PLLC; Mandy Wilson Decker; Gary N. Stewart

(57) ABSTRACT

The presently-disclosed subject matter describes fusion proteins comprising butyrylcholinesterase (BChE) having an improved production yield and biological half-life and nucleotides encoding the same.

13 Claims, 5 Drawing Sheets

Specification includes a Sequence Listing.

SEQUENCE LISTING

<160> NUMBER OF SEQ ID NOS: 37

<210> SEQ ID NO 1
<211> LENGTH: 30
<212> TYPE: DNA
<213> ORGANISM: Artificial Sequence
<220> FEATURE:
<223> OTHER INFORMATION: Recombinant

<400> SEQUENCE: 1
ccggcgccgg cgccgccggc gccggcgccg                                    30

<210> SEQ ID NO 2
<211> LENGTH: 10
<212> TYPE: PRT
<213> ORGANISM: Artificial Sequence
<220> FEATURE:
<223> OTHER INFORMATION: Recombinant

<400> SEQUENCE: 2

Pro Ala Pro Ala Pro Pro Ala Pro Ala Pro
1               5                   10

<210> SEQ ID NO 3
<211> LENGTH: 15
<212> TYPE: DNA
<213> ORGANISM: Artificial Sequence
<220> FEATURE:
<223> OTHER INFORMATION: Recombinant

<400> SEQUENCE: 3
ccggcgccgg cgccg                                                      15

<210> SEQ ID NO 4
<211> LENGTH: 5
<212> TYPE: PRT
<213> ORGANISM: Artificial Sequence
<220> FEATURE:
<223> OTHER INFORMATION: Recombinant

<400> SEQUENCE: 4

Pro Ala Pro Ala Pro
1               5

<210> SEQ ID NO 5
<211> LENGTH: 24
<212> TYPE: DNA
<213> ORGANISM: Artificial Sequence
<220> FEATURE:
<223> OTHER INFORMATION: Recombinant

<400> SEQUENCE: 5
ggcggcggca gcggcggcgg cagc                                            24

<210> SEQ ID NO 6
<211> LENGTH: 8
<212> TYPE: PRT
<213> ORGANISM: Artificial Sequence
<220> FEATURE:
<223> OTHER INFORMATION: Recombinant

<400> SEQUENCE: 6

Gly Gly Gly Ser Gly Gly Gly Ser
1               5

<210> SEQ ID NO 7
<211> LENGTH: 699
<212> TYPE: DNA
<213> ORGANISM: Artificial Sequence
<220> FEATURE:
<223> OTHER INFORMATION: Recombinant

<400> SEQUENCE: 7
gcagagccta agtcctgcga caaaactcac acatgcccac cgtgcccagc acctgaactc      60
ctggggggac cgtcagtctt cctcttcccc ccaaaaccca aggacaccct catgatctcc     120
cggacccctg aggtcacatg cgtggtggtg gacgtgagcc acgaagaccc tgaggtcaag     180
ttcaactggt acgtggacgg cgtggaggtg cataatgcca agacaaagcc gcgggaggag     240
cagtacaaca gcacgtaccg tgtggtcagc gtcctcaccg tcctgcacca ggactggctg     300
aatggcaagg agtacaagtg caaggtctcc aacaaagccc tcccagcccc catcgagaaa     360
accatctcca aagccaaagg gcagccccga gaaccacagg tgtacaccct gcccccatcc     420

| | | | | |
|---|---|---|---|---|
| cgggacgagc | tgaccaagaa | ccaggtcagc | ctgacctgcc | tggtcaaagg cttctatccc | 480 |
| agcgacatcg | ccgtggagtg | ggagagcaat | gggcagccgg | agaacaacta caagaccacg | 540 |
| cctcccgtgc | tggactccga | cggctccttc | ttcctctaca | gcaagctcac cgtggacaag | 600 |
| agcaggtggc | agcaggggaa | cgtcttctca | tgctccgtga | tgcacgaggc tctgcacaac | 660 |
| cactacacgc | agaagagcct | ctccctgtct | ccgggtaaa | | 699 |

```
<210> SEQ ID NO 8
<211> LENGTH: 233
<212> TYPE: PRT
<213> ORGANISM: Artificial Sequence
<220> FEATURE:
<223> OTHER INFORMATION: Recombinant

<400> SEQUENCE: 8

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 9
<211> LENGTH: 1722
<212> TYPE: DNA
<213> ORGANISM: Artificial Sequence
<220> FEATURE:
<223> OTHER INFORMATION: Recombinant

<400> SEQUENCE: 9
```

| | | | | |
|---|---|---|---|---|
| gaagatgaca | tcataattgc | aacaaagaat | ggaaaagtca | gagggatgaa cttgacagtt | 60 |
| tttggtggca | cggtaacagc | ctttcttgga | attccctatg | cacagccacc tcttggtaga | 120 |

```
cttcgattca aaaagccaca gtctctgacc aagtggtctg atatttggaa tgccacaaaa    180
tatgcaaatt cttgctgtca gaacatagat caaagttttc caggcttcca tggatcagag    240
atgtggaacc caaacactga cctcagtgaa gactgtttat atctaaatgt atggattcca    300
gcacctaaac caaaaaatgc cactgtattg atatggattt atggtggtgg ttttcaaact    360
ggaacatcat ctttacatgt ttatgatggc aagtttctgg ctcgggttga agagttatt    420 gtagtgtcaa tgaactatag ggtgggtgcc ctaggattct tagctttgcc aggaaatcct    480
gaggctccag ggaacatggg tttatttgat caacagttgg ctcttcagtg ggttcaaaaa    540
aatatagcag cctttggtgg aaatcctaaa agtgtaactc tctttggaga agtgcagga    600 gcagcttcag ttagcctgca tttgctttct cctggaagcc attcattgtt caccagagcc    660
attctgcaaa gtggttcctt taatgctcct tgggcggtaa catctcttta tgaagctagg    720
aacagaacgt gaacttagc taaattgact ggttgctcta gagagaatga gactgaaata    780
atcaagtgtc ttagaaataa agatccccaa gaaattcttc tgaatgaagc atttgttgtc    840
ccctatggga ctcctttgtc agtaaacttt ggtccgaccg tggatggtga ttttctcact    900
gacatgccag acatattact tgaacttgga caatttaaaa aaacccagat tttggtgggt    960
gttaataaag atgaagggac agcttttta gtctatggtg ctcctggctt cagcaaagat   1020
aacaatagta tcataactag aaaagaattt caggaaggtt taaaatatat ttttccagga   1080
gtgagtgagt ttggaaagga atccatcctt tttcattaca cagactgggt agatgatcag   1140
agacctgaaa actaccgtga ggccttgggt gatgttgttg gggattataa tttcatatgc   1200
cctgccttgg agttcaccaa gaagttctca gaatggggaa ataatgcctt tttctactat   1260
tttgaacacc gatcctccaa acttccgtgg ccagaatgga tgggagtgat gcatggctat   1320
gaaattgaat ttgtctttgg tttacctctg gaaagaagag ataattacac aaaagccgag   1380
gaaattttga gtagatccat agtgaaacgg tgggcaaatt ttgcaaaata tgggaatcca   1440
aatgagactc agaacaatag cacaagctgg cctgtcttca aaagcactga acaaaaatat   1500
ctaaccttga atacagagtc aacaagaata atgacgaaac tacgtgctca acaatgtcga   1560
ttctggacat cattttttcc aaaagtcttg gaaatgacag gaaatattga tgaagcagaa   1620
tgggagtgga agcaggatt ccatcgctgg aacaattaca tgatggactg gaaaaatcaa   1680
tttaacgatt acactagcaa gaaagaaagt tgtgtgggtc tc                       1722
```

<210> SEQ ID NO 10
<211> LENGTH: 574
<212> TYPE: PRT
<213> ORGANISM: Artificial Sequence
<220> FEATURE:
<223> OTHER INFORMATION: Recombinant

<400> SEQUENCE: 10

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80
```

```
Met Trp Asn Pro Asn Thr Asp Leu Ser Glu Asp Cys Leu Tyr Leu Asn
                85                  90                  95
Val Trp Ile Pro Ala Pro Lys Pro Lys Asn Ala Thr Val Leu Ile Trp
                100                 105                 110
Ile Tyr Gly Gly Gly Phe Gln Thr Gly Thr Ser Ser Leu His Val Tyr
                115                 120                 125
Asp Gly Lys Phe Leu Ala Arg Val Glu Arg Val Ile Val Val Ser Met
    130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
                180                 185                 190
Thr Leu Phe Gly Glu Ser Ala Gly Ala Ala Ser Val Ser Leu His Leu
                195                 200                 205
Leu Ser Pro Gly Ser His Ser Leu Phe Thr Arg Ala Ile Leu Gln Ser
210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Pro Leu Ser Val
                275                 280                 285
Asn Phe Gly Pro Thr Val Asp Gly Asp Phe Leu Thr Asp Met Pro Asp
                290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
                355                 360                 365
Ile Leu Phe His Tyr Thr Asp Trp Val Asp Asp Gln Arg Pro Glu Asn
                370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
                435                 440                 445
Pro Leu Glu Arg Arg Asp Asn Tyr Thr Lys Ala Glu Glu Ile Leu Ser
450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
```

-continued

```
Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
            515                 520                 525

Val Leu Glu Met Thr Gly Asn Ile Asp Glu Ala Glu Trp Glu Trp Lys
        530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 11
<211> LENGTH: 529
<212> TYPE: PRT
<213> ORGANISM: Artificial Sequence
<220> FEATURE:
<223> OTHER INFORMATION: Recombinant

<400> SEQUENCE: 11

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285
```

Asn Phe Gly Pro Thr Val Asp Gly Asp Phe Leu Thr Asp Met Pro Asp
            290                 295                 300

Ile Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val

<210> SEQ ID NO 12
<211> LENGTH: 574
<212> TYPE: PRT
<213> ORGANISM: Artificial Sequence
<220> FEATURE:
<223> OTHER INFORMATION: Recombinant

<400> SEQUENCE: 12

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
            195                 200                 205

Leu Ser Pro Gly Ser His Ser Leu Phe Thr Arg Ala Ile Leu Gln Ser
210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
            275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

-continued

```
Val Leu Glu Met Thr Gly Asn Ile Asp Glu Ala Glu Trp Glu Trp Lys
        530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570

<210> SEQ ID NO 13
<211> LENGTH: 529
<212> TYPE: PRT
<213> ORGANISM: Artificial Sequence
<220> FEATURE:
<223> OTHER INFORMATION: Recombinant

<400> SEQUENCE: 13

Glu Asp Asp Ile Ile Ile Ala Thr Lys Asn Gly Lys Val Arg Gly Met
1               5                   10                  15
Asn Leu Thr Val Phe Gly Gly Thr Val Thr Ala Phe Leu Gly Ile Pro
                20                  25                  30
Tyr Ala Gln Pro Pro Leu Gly Arg Leu Arg Phe Lys Lys Pro Gln Ser
            35                  40                  45
Leu Thr Lys Trp Ser Asp Ile Trp Asn Ala Thr Lys Tyr Ala Asn Ser
    50                  55                  60
Cys Cys Gln Asn Ile Asp Gln Ser Phe Pro Gly Phe His Gly Ser Glu
65                  70                  75                  80
Met Trp Asn Pro Asn Thr Asp Leu Ser Glu Asp Cys Leu Tyr Leu Asn
                85                  90                  95
Val Trp Ile Pro Ala Pro Lys Pro Lys Asn Ala Thr Val Leu Ile Trp
            100                 105                 110
Ile Tyr Gly Gly Gly Phe Gln Thr Gly Thr Ser Ser Leu His Val Tyr
        115                 120                 125
Asp Gly Lys Phe Leu Ala Arg Val Glu Arg Val Ile Val Val Ser Met
    130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ser Gly Ala Ala Ser Val Ser Leu His Leu
        195                 200                 205
Leu Ser Pro Gly Ser His Ser Leu Phe Thr Arg Ala Ile Leu Gln Ser
    210                 215                 220
Gly Ser Ala Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
            260                 265                 270
Leu Leu Asn Glu Ala Phe Val Val Pro Tyr Gly Thr Pro Leu Gly Val
        275                 280                 285
Asn Phe Gly Pro Thr Val Asp Gly Asp Phe Leu Thr Asp Met Pro Asp
    290                 295                 300
Ile Leu Leu Glu Leu Gly Gln Phe Lys Lys Thr Gln Ile Leu Val Gly
305                 310                 315                 320
```

```
Val Asn Lys Asp Glu Gly Thr Trp Phe Leu Val Gly Gly Ala Pro Gly
            325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
            405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
            485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val

<210> SEQ ID NO 14
<211> LENGTH: 529
<212> TYPE: PRT
<213> ORGANISM: Artificial Sequence
<220> FEATURE:
<223> OTHER INFORMATION: Recombinant

<400> SEQUENCE: 14

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
        50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
            85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
            130                 135                 140
```

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
            165                 170                 175

Trp Val Gln Lys Asn Ile Ala Ala Phe Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Ala Leu Gly Val
        275                 280                 285

Asn Phe Gly Pro Thr Val Asp Gly Asp Phe Leu Thr Asp Met Pro Asp
    290                 295                 300

Ile Leu Glu Leu Gly Gln Phe Lys Lys Thr Gln Ile Leu Val Gly
305                 310                 315                 320

Val Asn Lys Asp Glu Gly Thr Trp Phe Leu Val Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val

<210> SEQ ID NO 15
<211> LENGTH: 529
<212> TYPE: PRT

<213> ORGANISM: Artificial Sequence
<220> FEATURE:
<223> OTHER INFORMATION: Recombinant

<400> SEQUENCE: 15

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Gln Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380
```

```
Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Pro Lys
                515                 520                 525

Val

<210> SEQ ID NO 16
<211> LENGTH: 233
<212> TYPE: PRT
<213> ORGANISM: Artificial Sequence
<220> FEATURE:
<223> OTHER INFORMATION: Recombinant

<400> SEQUENCE: 16

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205
```

Phe Ser Cys Ser Val Met His Glu Ala Leu His Asn His Tyr Thr Gln
        210                 215                 220

Lys Ser Leu Ser Leu Ser Pro Gly Lys
225                 230

<210> SEQ ID NO 17
<211> LENGTH: 232
<212> TYPE: PRT
<213> ORGANISM: Artificial Sequence
<220> FEATURE:
<223> OTHER INFORMATION: Recombinant

<400> SEQUENCE: 17

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Tyr Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 18
<211> LENGTH: 232
<212> TYPE: PRT
<213> ORGANISM: Artificial Sequence
<220> FEATURE:
<223> OTHER INFORMATION: Recombinant

<400> SEQUENCE: 18

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Tyr Ile Thr Arg Glu Pro Glu Val Thr Cys Val Val
        35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 19
<211> LENGTH: 5
<212> TYPE: PRT
<213> ORGANISM: Artificial Sequence
<220> FEATURE:
<223> OTHER INFORMATION: Recombinant

<400> SEQUENCE: 19

Glu Ala Ala Ala Lys
1               5

<210> SEQ ID NO 20
<211> LENGTH: 41
<212> TYPE: PRT
<213> ORGANISM: Artificial Sequence
<220> FEATURE:
<223> OTHER INFORMATION: Recombinant

<400> SEQUENCE: 20

Gly Thr Cys Thr Cys Gly Gly Gly Thr Ala Ala Gly Ala Gly
1               5                   10                  15

Gly Cys Thr Gly Cys Cys Gly Cys Ala Ala Gly Gly Ala Ala Gly
            20                  25                  30

Ala Thr Gly Ala Cys Ala Thr Cys Ala
        35                  40

<210> SEQ ID NO 21
<211> LENGTH: 36
<212> TYPE: PRT
<213> ORGANISM: Artificial Sequence
<220> FEATURE:
<223> OTHER INFORMATION: Recombinant

<400> SEQUENCE: 21

Cys Thr Thr Gly Gly Cys Gly Gly Cys Ala Gly Cys Cys Thr Cys Thr
1               5                   10                  15

Thr Thr Ala Cys Cys Cys Gly Gly Ala Gly Ala Cys Ala Gly Gly Gly
            20                  25                  30

Ala Gly Ala Gly
        35

<210> SEQ ID NO 22
<211> LENGTH: 40
<212> TYPE: PRT
<213> ORGANISM: Artificial Sequence
<220> FEATURE:
<223> OTHER INFORMATION: Recombinant

<400> SEQUENCE: 22

Gly Thr Cys Thr Cys Cys Gly Gly Gly Thr Ala Ala Cys Cys Thr
1               5                   10                  15

Gly Cys Thr Cys Cys Ala Gly Cys Cys Cys Gly Gly Ala Ala Gly
            20                  25                  30

Ala Thr Gly Ala Cys Ala Thr Cys
        35                  40

<210> SEQ ID NO 23
<211> LENGTH: 36
<212> TYPE: PRT
<213> ORGANISM: Artificial Sequence
<220> FEATURE:
<223> OTHER INFORMATION: Recombinant

<400> SEQUENCE: 23

Cys Gly Gly Gly Gly Cys Thr Gly Gly Ala Gly Cys Ala Gly Gly Thr
1               5                   10                  15

Thr Thr Ala Cys Cys Cys Gly Gly Ala Gly Ala Cys Ala Gly Gly Gly
            20                  25                  30

Ala Gly Ala Gly
        35

<210> SEQ ID NO 24
<211> LENGTH: 50
<212> TYPE: PRT
<213> ORGANISM: Artificial Sequence
<220> FEATURE:
<223> OTHER INFORMATION: Recombinant

<400> SEQUENCE: 24

Gly Thr Cys Thr Cys Cys Gly Gly Gly Thr Ala Ala Ala Gly Gly Thr
1               5                   10                  15

Gly Gly Ala Gly Gly Thr Thr Cys Cys Gly Gly Thr Gly Gly Ala Gly
            20                  25                  30

Gly Thr Thr Cys Cys Gly Ala Ala Gly Ala Thr Gly Ala Cys Ala Thr
        35                  40                  45

Cys Ala
    50

<210> SEQ ID NO 25
<211> LENGTH: 45
<212> TYPE: PRT
<213> ORGANISM: Artificial Sequence
<220> FEATURE:
<223> OTHER INFORMATION: Recombinant

<400> SEQUENCE: 25

Gly Gly Ala Ala Cys Cys Thr Cys Cys Ala Cys Gly Gly Ala Ala
1               5                   10                  15

Cys Cys Thr Cys Cys Ala Cys Cys Thr Thr Ala Cys Cys Cys Gly
                20                  25                  30

Gly Ala Gly Ala Cys Ala Gly Gly Gly Ala Gly Ala Gly
            35                  40                  45

<210> SEQ ID NO 26
<211> LENGTH: 55
<212> TYPE: PRT
<213> ORGANISM: Artificial Sequence
<220> FEATURE:
<223> OTHER INFORMATION: Recombinant

<400> SEQUENCE: 26

Gly Thr Cys Thr Cys Cys Gly Gly Gly Thr Ala Ala Cys Cys Thr
1               5                   10                  15

Gly Cys Thr Cys Cys Ala Gly Cys Cys Cys Gly Cys Cys Thr Gly
                20                  25                  30

Cys Thr Cys Cys Ala Gly Cys Cys Cys Gly Gly Ala Ala Gly Ala
            35                  40                  45

Thr Gly Ala Cys Ala Thr Cys
        50                  55

<210> SEQ ID NO 27
<211> LENGTH: 51
<212> TYPE: PRT
<213> ORGANISM: Artificial Sequence
<220> FEATURE:
<223> OTHER INFORMATION: Recombinant

<400> SEQUENCE: 27

Cys Gly Gly Gly Gly Cys Thr Gly Gly Ala Gly Cys Ala Gly Cys
1               5                   10                  15

Gly Gly Gly Gly Cys Thr Gly Gly Ala Gly Cys Ala Gly Gly Thr Thr
                20                  25                  30

Thr Ala Cys Cys Cys Gly Gly Ala Gly Ala Cys Ala Gly Gly Gly Ala
            35                  40                  45

Gly Ala Gly
        50

<210> SEQ ID NO 28
<211> LENGTH: 233
<212> TYPE: PRT
<213> ORGANISM: Artificial Sequence
<220> FEATURE:
<223> OTHER INFORMATION: Recombinant

<400> SEQUENCE: 28

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Gln Val Lys Phe Asn Trp Tyr
        50                  55                  60

Val Asp Gly Val Gln Val His Asn Ala Lys Thr Lys Pro Arg Glu Gln
65                  70                  75                  80

Gln Tyr Asn Ser Thr Tyr Arg Val Val Ser Val Leu Thr Val Leu His
                85                  90                  95

Gln Asn Trp Leu Asp Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 29
<211> LENGTH: 233
<212> TYPE: PRT
<213> ORGANISM: Artificial Sequence
<220> FEATURE:
<223> OTHER INFORMATION: Recombinant

<400> SEQUENCE: 29

Gln Glu Pro Lys Ser Ser Asp Lys Thr His Thr Ser Pro Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
            210                 215                 220

Lys Ser Leu Ser Leu Ser Pro Gly Lys
225                 230

<210> SEQ ID NO 30
<211> LENGTH: 233
<212> TYPE: PRT
<213> ORGANISM: Artificial Sequence
<220> FEATURE:
<223> OTHER INFORMATION: Recombinant

<400> SEQUENCE: 30

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Glu Pro Glu Val Thr Cys Val
            35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Glu Glu Met
            130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
            210                 215                 220

Lys Ser Leu Ser Leu Ser Pro Gly Lys
225                 230

<210> SEQ ID NO 31
<211> LENGTH: 233
<212> TYPE: PRT
<213> ORGANISM: Artificial Sequence
<220> FEATURE:
<223> OTHER INFORMATION: Recombinant

<400> SEQUENCE: 31

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Tyr Ile Thr Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 32
<211> LENGTH: 233
<212> TYPE: PRT
<213> ORGANISM: Artificial Sequence
<220> FEATURE:
<223> OTHER INFORMATION: Recombinant

<400> SEQUENCE: 32

Gln Glu Pro Lys Ser Ser Asp Lys Thr His Thr Ser Pro Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Tyr Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

```
Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 33
<211> LENGTH: 233
<212> TYPE: PRT
<213> ORGANISM: Artificial Sequence
<220> FEATURE:
<223> OTHER INFORMATION: Recombinant

<400> SEQUENCE: 33

Gln Glu Pro Lys Ser Ser Asp Lys Thr His Thr Ser Pro Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Tyr Ile Thr Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 34
<211> LENGTH: 233
<212> TYPE: PRT
<213> ORGANISM: Artificial Sequence
```

```
<220> FEATURE:
<223> OTHER INFORMATION: Recombinant

<400> SEQUENCE: 34

Gln Glu Pro Lys Ser Ser Asp Lys Thr His Thr Ser Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Tyr Ile Thr Arg Glu Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 35
<211> LENGTH: 762
<212> TYPE: PRT
<213> ORGANISM: Artificial Sequence
<220> FEATURE:
<223> OTHER INFORMATION: Recombinant

<400> SEQUENCE: 35

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95
```

```
Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
            130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
            210                 215                 220

Lys Ser Leu Ser Leu Ser Pro Gly Lys Glu Asp Asp Ile Ile Ile Ala
225                 230                 235                 240

Thr Lys Asn Gly Lys Val Arg Gly Met Asn Leu Thr Val Phe Gly Gly
            245                 250                 255

Thr Val Thr Ala Phe Leu Gly Ile Pro Tyr Ala Gln Pro Pro Leu Gly
            260                 265                 270

Arg Leu Arg Phe Lys Lys Pro Gln Ser Leu Thr Lys Trp Ser Asp Ile
            275                 280                 285

Trp Asn Ala Thr Lys Tyr Ala Asn Ser Cys Cys Gln Asn Ile Asp Gln
            290                 295                 300

Ser Phe Pro Gly Phe His Gly Ser Glu Met Trp Asn Pro Asn Thr Asp
305                 310                 315                 320

Leu Ser Glu Asp Cys Leu Tyr Leu Asn Val Trp Ile Pro Ala Pro Lys
            325                 330                 335

Pro Lys Asn Ala Thr Val Leu Ile Trp Ile Tyr Gly Gly Gly Phe Gln
            340                 345                 350

Thr Gly Thr Ser Ser Leu His Val Tyr Asp Gly Lys Phe Leu Ala Arg
            355                 360                 365

Val Glu Arg Val Ile Val Val Ser Met Asn Tyr Arg Val Gly Ala Leu
            370                 375                 380

Gly Phe Leu Ala Leu Pro Gly Asn Pro Glu Ala Pro Gly Asn Met Gly
385                 390                 395                 400

Leu Phe Asp Gln Gln Leu Ala Leu Gln Trp Val Gln Lys Asn Ile Ala
            405                 410                 415

Ala Phe Gly Gly Asn Pro Lys Ser Val Thr Leu Phe Gly Glu Ser Ala
            420                 425                 430

Gly Ala Ala Ser Val Ser Leu His Leu Leu Ser Pro Gly Ser His Ser
            435                 440                 445

Leu Phe Thr Arg Ala Ile Leu Gln Ser Gly Ser Phe Asn Ala Pro Trp
            450                 455                 460

Ala Val Thr Ser Leu Tyr Glu Ala Arg Asn Arg Thr Leu Asn Leu Ala
465                 470                 475                 480

Lys Leu Thr Gly Cys Ser Arg Glu Asn Glu Thr Glu Ile Ile Lys Cys
            485                 490                 495

Leu Arg Asn Lys Asp Pro Gln Glu Ile Leu Leu Asn Glu Ala Phe Val
            500                 505                 510
```

```
Val Pro Tyr Gly Thr Pro Leu Ser Val Asn Phe Gly Pro Thr Val Asp
            515                 520                 525

Gly Asp Phe Leu Thr Asp Met Pro Asp Ile Leu Leu Glu Leu Gly Gln
        530                 535                 540

Phe Lys Lys Thr Gln Ile Leu Val Gly Val Asn Lys Asp Glu Gly Thr
545                 550                 555                 560

Ala Phe Leu Val Tyr Gly Ala Pro Gly Phe Ser Lys Asp Asn Asn Ser
                565                 570                 575

Ile Ile Thr Arg Lys Glu Phe Gln Glu Gly Leu Lys Ile Phe Phe Pro
            580                 585                 590

Gly Val Ser Glu Phe Gly Lys Glu Ser Ile Leu Phe His Tyr Thr Asp
        595                 600                 605

Trp Val Asp Asp Gln Arg Pro Glu Asn Tyr Arg Glu Ala Leu Gly Asp
    610                 615                 620

Val Val Gly Asp Tyr Asn Phe Ile Cys Pro Ala Leu Glu Phe Thr Lys
625                 630                 635                 640

Lys Phe Ser Glu Trp Gly Asn Asn Ala Phe Phe Tyr Tyr Phe Glu His
                645                 650                 655

Arg Ser Ser Lys Leu Pro Trp Pro Glu Trp Met Gly Val Met His Gly
            660                 665                 670

Tyr Glu Ile Glu Phe Val Phe Gly Leu Pro Leu Glu Arg Arg Asp Asn
        675                 680                 685

Tyr Thr Lys Ala Glu Glu Ile Leu Ser Arg Ser Ile Val Lys Arg Trp
    690                 695                 700

Ala Asn Phe Ala Lys Tyr Gly Asn Pro Asn Glu Thr Gln Asn Asn Ser
705                 710                 715                 720

Thr Ser Trp Pro Val Phe Lys Ser Thr Glu Gln Lys Tyr Leu Thr Leu
                725                 730                 735

Asn Thr Glu Ser Thr Arg Ile Met Thr Lys Leu Arg Ala Gln Gln Cys
            740                 745                 750

Arg Phe Trp Thr Ser Phe Phe Pro Lys Val
        755                 760

<210> SEQ ID NO 36
<211> LENGTH: 10
<212> TYPE: PRT
<213> ORGANISM: Artificial Sequence
<220> FEATURE:
<223> OTHER INFORMATION: Recombinant

<400> SEQUENCE: 36

Gly Gly Gly Gly Ser Gly Gly Gly Gly Ser
1               5                   10

<210> SEQ ID NO 37
<211> LENGTH: 14
<212> TYPE: PRT
<213> ORGANISM: Artificial Sequence
<220> FEATURE:
<223> OTHER INFORMATION: G6S

<400> SEQUENCE: 37

Gly Gly Gly Gly Gly Gly Ser Gly Gly Gly Gly Gly Gly Ser
1               5                   10
```

INCREASED POLYPEPTIDE PRODUCTION YIELDS OF BUTYRYLCHOLINESTERASE POLYPEPTIDES FOR THERAPEUTIC USE

RELATED APPLICATIONS

This application claims priority from U.S. Provisional Patent Application No. 62/950,765 filed on Dec. 19, 2019 the entire disclosure of which is incorporated herein by this reference.

GOVERNMENT INTEREST

This invention was made with government support under Grant Numbers DA041115, DA035552, DA032910, DA013930, and DA025100 awarded by the National Institutes of Health (NIH). The government has certain rights in the invention.

SEQUENCE LISTING

This application contains a sequence listing submitted in accordance with 37 C.F.R. 1.821, named 13177N 2396US ZHAN sequence listing.txt, created on Dec. 21, 2020, having a size of 67,608 bytes, which is incorporated herein by this reference.

TECHNICAL FIELD

The presently-disclosed subject matter relates to fusion proteins comprising butyrylcholinesterase (BChE) and having an improved production yield and biological half-life.

BACKGROUND

Human plasma butyrylcholinesterase (BChE) has a long history of clinical application, without any adverse events reported [1]. Two clinical trials (NCT00333515 and NCT00333528) of BChE protein were performed by Baxter Healthcare Corporation, showing that recombinant human BChE is also safe for use in humans.

It has been well known that BChE can intercept and destroy the organophosphorus (OP) nerve poisons before they reach their target—acetylcholinesterase (AChE) [1-3]. Thus, administration of BChE is recognized as an effective and safe medication for the prevention of organophosphorus (OP) nerve agent toxicity [3-6].

Because of the stoichiometric binding of BChE with OP nerve agent, a large amount of BChE protein is required to achieve its nerve protective effects in vivo. Thus, without an efficient BChE expression method, the clinical application of BChE is severely impeded by its actual availability, since the quantity of BChE protein purified from human plasma is very limited. Hence, it is highly desired to develop methods that can be used to efficiently produce BChE in a large-scale for further preclinical and clinical development.

Another driving force to solve this protein production problem comes from the potential application of mutant BChE for treatment of cocaine abuse. BChE is a major metabolic enzyme that catalyzes the hydrolysis of cocaine to produce biologically inactive metabolites. Unfortunately, the catalytic efficiency ($k_{cat}/K_M$) of wild-type BChE against naturally occurring (−)-cocaine is too low ($k_{cat}$=4.1 min$^{-1}$ and $K_M$=4.5 µM) [7] to be effective for accelerating cocaine metabolism. Through structure and mechanism based computational design and wet experimental tests, a series of human BChE mutants with significantly improved catalytic efficiency against cocaine have been designed and discovered [7-12]. These BChE mutants have been recognized as true cocaine hydrolases (CocHs) in literature [8] when they have at least 1,000-fold improved catalytic efficiency against (−)-cocaine compared to wild-type human BChE [9-12].

The CocH-based approach has been recognized as a truly promising strategy for treatment of cocaine overdose and addiction [8, 13-15]. Thus, it is critical for further preclinical and clinical development towards the actual use of a BChE mutant in clinical practice to improve the protein production efficiency of the BChE and its mutants.

In fact, extensive efforts have been made to improve the protein production, with the goal to economically produce recombinant human BChE or BChE mutants. Expression in bacteria is recognized as the most economical method for producing recombinant proteins, but wild-type BChE expressed in bacteria cannot fold appropriately to become an active enzyme [16]. BChE proteins expressed in silkworm and insect cells were proven to be active [17, 18], but their pharmacokinetic profiles have not been characterized. Transgenic plants and animals were also generated to produce BChE or CocHs with a significantly improved efficiency, but the proteins produced usually have significantly shorter biological half-lives [19-22]. The short biological half-life is mainly explained by possibly incomplete post-translational modification causing the BChE or CocH to be taken up by asialo receptors in the liver [1].

Compared to all the expression systems above, CHO (Chinese-hamster ovary) cells provide more consistently proper protein post-translational modification [23]. Considering that the improper post-translational modification would not only shorten the protein's biological half-life, but also increase the risk of immunogenicity as an improper glycan structure might cause the protein to be recognized as an immunogen [1], CHO cells might be the most propriate system to produce the desirably safe and effective BChE (or BChE mutant) with a relatively long biological half-life. However, the biological half-life of the recombinant BChE or mutant produced in CHO [19-22, 24, 25] is still much shorter than that of native BChE. For example, CocH3 produced in CHO cells has a biological half-life of 7.3 hr in rats, which is considerably longer than that (~13 min) of CocH3 expressed in plants [19, 24], but it is still much shorter than that (43 hr) of native BChE [26]. In addition, the low expression yield of BChE or its mutant in CHO cells is another major problem.

Thus, there remains a need in the art to efficiently produce active recombinant BChE and CocHs with a sufficiently long biological half-life The presently disclosed subject matter identifies fusion proteins comprising BChE polypeptides that not only have a long biological half-life, but also a significantly-improved yield of protein production. Such polypeptides have utility in therapeutic treatment, for example, treatment of cocaine overdose and addiction, and treatment of OP detoxication.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes fusion proteins comprising butyrylcholinesterase (BChE) and having an improved production yield and biological half-life, and methods for production of such fusion proteins.

One embodiment of the present invention is a polypeptide molecule, comprising: an Fc polypeptide joined to an N-terminal end of a butyrylcholinesterase (BChE) polypeptide. In other embodiments of the present invention, an Fc polypeptide is joined to a C-terminal end of a butyrylcholinesterase (BChE) polypeptide. In some embodiments of the present invention, the Fc polypeptide is optionally joined to the BChE polypeptide via a linker, the linker comprising a sequence selected from the sequences of SEQ ID NO: 2, SEQ ID NO: 4, SEQ ID NO: 6, SEQ ID NO: 19, SEQ ID NO: 36, and SEQ ID NO: 37. In certain embodiments of the present invention, the Fc polypeptide has the sequence of SEQ ID NO: 8, or a fragment thereof, wherein the Fc polypeptide or fragment thereof includes 3 to 8 amino acid substitutions at 3 to 8 of residues selected from 1, 6, 12, 15, 24, 38, 40, 42, 58, 69, 80, 98, 101, 142, and 144. In further embodiments of the present invention, the Fc polypeptide is a fragment wherein 1, 2, 3, 4, 5, 6, 7, 8, 9, 10, 11, 12, 13, 14, 15, or 16 amino acids are removed from the N-terminus of SEQ ID NO: 8. In some embodiments, the Fc polypeptide includes mutations as set forth in Table A, relative to SEQ ID NO: 8.

TABLE A

Substitutions relative to SEQ ID NO: 8 for exemplary Fc Polypeptides

| Fc | 1 | 6 | 12 | 15 | 24 | 38 | 40 | 42 | 58 | 69 | 80 | 98 | 101 | 142 | 144 |
|---|---|---|---|---|---|---|---|---|---|---|---|---|---|---|---|
| M3 | A1V | | | | | | | | | | | | | D124E | L144M |
| M8 | A1V | | | | | | | | E58Q | E69Q | E80Q | D98N | N101D | D124E | L144M |
| M5 | A1Q | C6S | C12S | C15S | P24S | | | | | | | | | D142E | L144M |
| M4 | A1V | | | | | M38Y | | | | | | | | D142E | L144M |
| M4' | A1V | | | | | | | T42E | | | | | | D142E | L144M |
| M5' | A1V | | | | | M38Y | S40T | | | | | | | D142E | L144M |
| M6 | A1V | | | | | M38Y | S40T | T42E | | | | | | D142E | L144M |
| M6' | A1Q | C6S | C12S | C15S | P24S | M38Y | | | | | | | | | |
| M7 | A1Q | C6S | C12S | C15S | P24S | M38Y | S40T | | | | | | | | |
| M8' | A1Q | C6S | C12S | C15S | P24S | M38Y | S40T | T42E | | | | | | | |

In some embodiments, the BChE polypeptide is an BChE polypeptide fragment that further includes amino acid substitutions as set forth in Table B, relative to SEQ ID NO: 10.

TABLE B

Substitutions relative to SEQ ID NO: 10 for exemplary BChE Polypeptides

| 199 | 227 | 285 | 286 | 287 | 328 | 332 | 441 |
|---|---|---|---|---|---|---|---|
| A199S | | | | | A328W | Y332G | |
| A199S | F227A | | | | A328W | Y332G | |
| A199S | | | | S287G | A328W | Y332G | |
| A199S | F227A | | | S287G | A328W | Y332G | |
| A199S | F227A | | | S287G | A328W | | E441D |
| A199S | F227A | P285A | | S287G | A328W | Y332G | |
| A199S | F227A | P285S | | S287G | A328W | Y332G | |
| A199S | F227A | P285Q | | S287G | A328W | Y332G | |
| A199S | F227P | | | S287G | A328W | Y332G | |
| A199S | F227A | | L286M | S287G | A328W | Y332G | |
| A199S | | P285Q | | S287G | A328W | Y332G | |
| A199S | | P285I | | S287G | A328W | Y332G | |
| A199S | F227G | | | S287G | A328W | Y332G | |
| A199S | | P285S | | S287G | A328W | Y332G | |
| A199S | F227V | | | S287G | A328W | Y332G | |
| A199S | | P285G | | S287G | A328W | Y332G | |
| A199S | F227I | | | S287G | A328W | Y332G | |
| A199S | F227L | | | S287G | A328W | Y332G | |
| A199S | | P286M | L286M | S287G | A328W | Y332G | |
| A199S | F227A | | | S287G | A328W | Y332G | |
| A199S | F227S | — | — | S287G | A328W | Y332G | — |
| A199S | F227T | — | — | S287G | A328W | Y332G | — |
| A199S | F227M | — | — | S287G | A328W | Y332G | — |
| A199S | F227C | — | — | S287G | A328W | Y332G | — |
| A199S | F227A | P285N | — | S287G | A328W | Y332G | — |
| A199S | F227P | P285A | — | S287G | A328W | Y332G | — |
| A199S | F227S | P285Q | — | S287G | A328W | Y332G | — |
| A199S | F227S | P285S | — | S287G | A328W | Y332G | — |
| A199S | F227S | P285G | — | S287G | A328W | Y332G | — |
| A199S | F227P | P285S | L286M | S287G | A328W | Y332G | — |
| A199S | F227A | P285S | — | S287G | A328W | — | E441D |
| A199S | F227A | P285A | — | S287G | A328W | — | E441D |
| A199S | F227P | — | L286M | S287G | A328W | Y332G | — |
| A199S | F227G | P285A | — | S287G | A328W | Y332G | — |
| A199S | F227G | P285G | — | S287G | A328W | Y332G | — |
| A199S | F227G | P285Q | — | S287G | A328W | Y332G | — |
| A199S | F227G | P285S | — | S287G | A328W | Y332G | — |
| A199S | F227A | P285E | — | S287G | A328W | Y332G | — |
| A199S | F227P | P285N | — | S287G | A328W | Y332G | — |
| A199S | F227S | P285A | — | S287G | A328W | Y332G | — |
| A199S | F227S | P285N | — | S287G | A328W | Y332G | — |
| A199S | F227S | — | L286M | S287G | A328W | Y332G | — |
| A199S | F227G | — | L286M | S287G | A328W | Y332G | — |

In some embodiments of the present invention, the Fc polypeptide is selected from SEQ ID NO: 16, SEQ ID NO: 17, SEQ ID NO: 18, SEQ ID NO: 28, SEQ ID NO: 29, SEQ ID NO: 30, SEQ ID NO: 31, SEQ ID NO: 32, SEQ ID NO: 33, and SEQ ID NO: 34. In further embodiments, the BChE polypeptide has the sequence of SEQ ID NO: 10 or a fragment thereof, wherein the BChE polypeptide or fragment thereof includes 3 to 8 amino acid substitutions at 3 to 8 of residues chosen from 199, 227, 285, 286, 287, 328, 332, and 441. In other embodiments, the BChE polypeptide has a group of amino acid substitutions selected from A199S, F227A, F227S, F227Q, F227I, F227G, F227V, F227I, F227L, F227S, F227T, F227M, F227C, P285A, P285S, P285Q, P285I, P285G, P285M, P285N, P285E, S287G, A328W, Y332G, E441D, and combinations thereof. In other embodiments of the presently disclosed matter, the BChE polypeptide is a fragment wherein from 1 to 116 amino acids are removed from the N-terminus of SEQ ID NO: 10. In some embodiments of the invention, the BChE polypeptide is a fragment wherein from 1 to 432 amino acids are removed from the C-terminus of SEQ ID NO: 10. In some embodiments, the BChE polypeptide has a group of amino acid substitutions selected from A199S, F227A, F227S, F227Q, F227I, F227G, F227V, F227I, F227L, F227S, F227T, F227M, F227C, P285A, P285S, P285Q, P285I, P285G, P285M, P285N, P285E, S287G, A328W, Y332G, E441D, and combinations thereof. In other embodiments of the present invention, the transient expression level of the polypeptide is at least about 9 times higher than a reference BChE polypeptide that does not include the Fc polypeptide and linker. In some embodiments of the present invention, the polypeptide molecule is the polypeptide of SEQ ID NO: 35. In other embodiments, the BChE polypeptide is selected from: SEQ ID NO: 12, SEQ ID NO: 13, SEQ ID NO: 14, and SEQ ID NO: 15. In further embodiments, Fc polypeptide is selected from SEQ ID NO: 16, SEQ ID NO: 17, and SEQ ID NO: 18.

The presently-disclosed subject matter also relates to a nucleotide molecule, comprising: a nucleotide encoding an Fc polypeptide joined by a nucleotide encoding a linker to a 5' end of a nucleotide encoding a butyrylcholinesterase (BChE) polypeptide. In some embodiments, the nucleotide encoding the linker comprises a sequence chosen from the sequences of SEQ ID NO: 1, SEQ ID NO: 3, and SEQ ID NO: 5. In some embodiments, the nucleotide encoding the Fc polypeptide has the sequence of SEQ ID NO: 7 or a fragment thereof, wherein the Fc polypeptide or fragment thereof includes 3 to 8 amino acid substitutions at 3 to 8 of residues chosen from 1, 6, 12, 15, 24, 38, 40, 42, 58, 69, 80, 98, 101, 142, and 144 relative to SEQ ID NO: 8. In further embodiments, the nucleotide encoding the BChE polypeptide has the sequence of SEQ ID NO: 9 or a fragment thereof, wherein the BChE polypeptide or fragment thereof includes 3 to 8 amino acid substitutions at 3 to 8 of residues chosen from 199, 227, 285, 286, 287, 328, 332, and 441 relative to SEQ ID NO: 10. In some embodiments of the present invention, the nucleotide molecule is within an expression vector.

The present invention also relates to a method of producing a polypeptide molecule including a BChE polypeptide, comprising: (a) providing in a vector a nucleotide sequence chosen from (i) a nucleotide sequence encoding the polypeptide molecule of claim 1, or (ii) a nucleotide sequence of claim 14; and (b) transfecting cells with the vector and allowing the cells to express the polypeptide molecule; and (c) isolating the polypeptide molecule. In further embodiments, there is at least about a 9-fold improvement in the yield of expression of the polypeptide molecule as compared to expression of a reference BChE polypeptide.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

Figure 1:
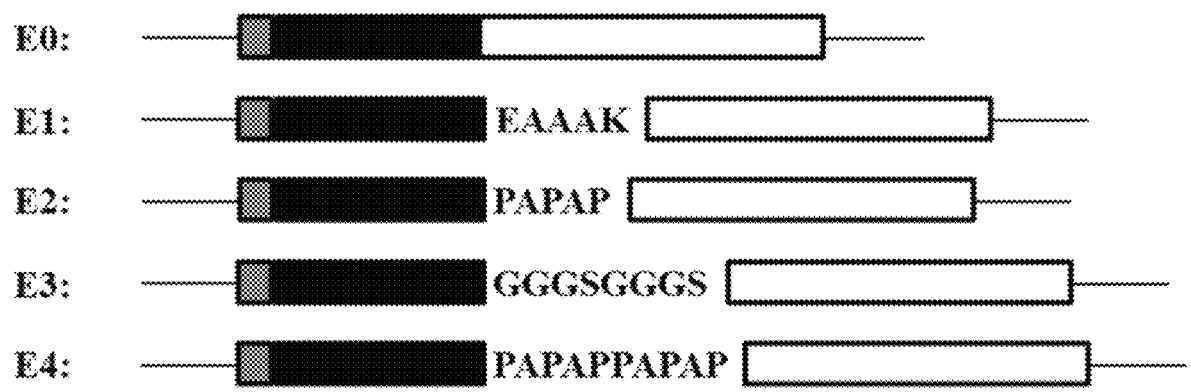
FIG. 1 includes a schematic illustrating four Fc-fused protein with various linkers (E1 with SEQ ID NO: 19; E2 with SEQ ID NO: 4; E3 with SEQ ID NO: 6; and E4 with SEQ ID NO: 2), as well as a non-linked Fc-BChE. The small grey box represents an IL-2 secretion signal peptide; the black box represents the sequence of a Fc polypeptide, as disclosed herein; and the white box represents the sequence of a BChE polypeptide, as disclosed herein.
Figure 2:
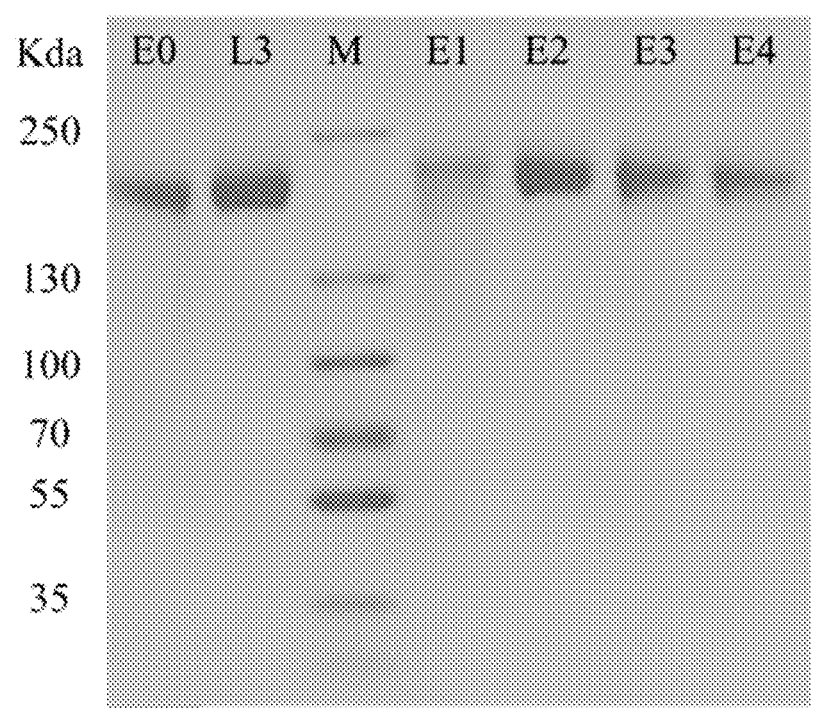
FIG. 2 includes a Coomassie-Blue stained native electrophoresis gel of purified fusion proteins, showing that the native structures of all fusion proteins exist in a dimer.
Figure 3:
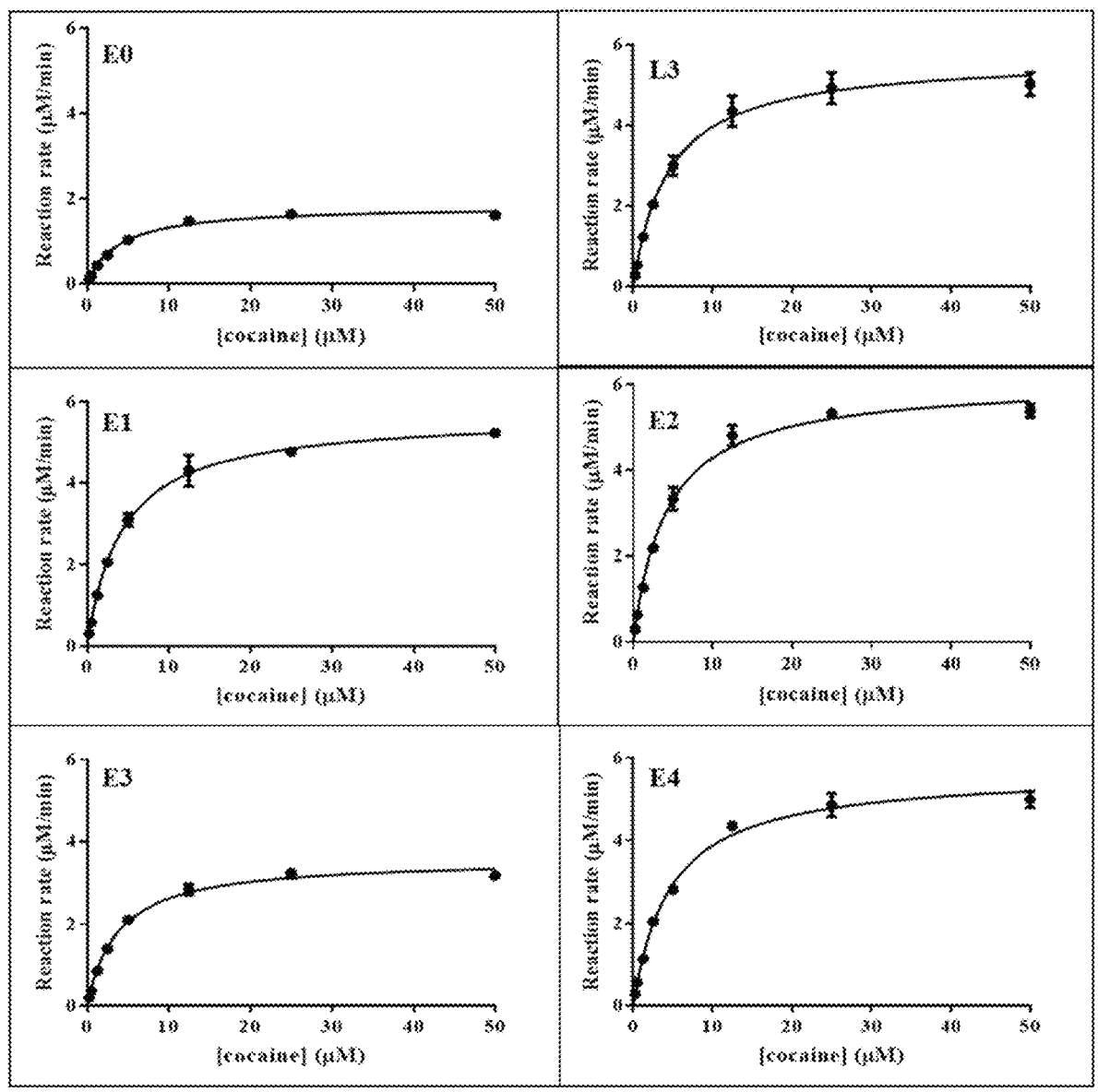
FIG. 3 includes kinetic data obtained in vitro for (−)-cocaine hydrolysis catalyzed by the fusion proteins. The reaction rate is represented in $\mu M$ min' per nM enzyme.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a biomarker" includes a plurality of such biomarkers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" refers to a subject afflicted with a disease or disorder. The term "patient" includes human and veterinary subjects.

As used herein, the term "BChE polypeptide" can refer to various mutations and truncations of the BChE protein including the mutations that are characterized by cocaine hydrolase (CoCH). BChE polypeptide for example includes, but it not limited to, SEQ ID NO: 10, SEQ ID NO: 11, SEQ ID NO: 12, SEQ ID NO: 13, SEQ ID NO: 14, and SEQ ID NO: 15.

EXAMPLES

The fusion proteins as disclosed herein were designed in view of a number of considerations. For example, they make use of a protein that is normally expressed in a high level as the N-terminal fusion partner to improve the expression of protein of interest [27, 28]. It was contemplated that the N-terminal fusion partner could "fool" the cellular process into expressing the fusion protein at a high level [28]. For another example, human IgG has a very long biological half-life ($t_{1/2}$). The fragment crystallizable (Fc) region of IgG binds to the neonatal Fc receptor (FcRn) in the acidic environment of the endosome and later is transported to the cell surface where, upon exposure to a neutral pH, IgG is released back into the main bloodstream [29]. In addition, IgG is the most common type of antibody found in the circulation, and can be expressed in CHO cells with a yield of more than 1 g/L [30].

The present inventors sought to design a long-acting CocH form which has not only a prolonged biological half-life without affecting the catalytic activity, but also an improved expression level in CHO cells. For this purpose, exemplary embodiments were prepared for testing, starting from CocH3 (the A199S/F227A/S287G/A328W/Y332G mutant [9] of human BChE) (SEQ ID NO: 12), a IL-2 signal peptide followed by Fc(M3) (the A1V/D142E/L144M mutant [31] of Fc)(SEQ ID NO: 16), which was fused with the N-terminal of CocH3 (SEQ ID NO: 12). Then the tetramerization domain (amino-acid residues 530 to 574) of CocH3 was deleted to minimize the possibility of affecting the correct folding of Fc(M3) or CocH3. On the other hand, it was contemplated that the presence of Fc(M3) might break the tetramer structure, resulting in a long and flexible peptide, which could be proteolyzed easily. In addition, according to computational modeling (data not shown), directly fusing Fc(M3) with the N-terminal of CocH3 could affect the entrance of substrate to the active site of CocH3, thus affecting the catalytic activity of CocH3. Hence, several types of linkers were selected and inserted between Fc(M3) and CocH3. In this way, various Fc(M3)-linker-CocH3 entities were prepared and tested for their catalytic activity against cocaine, protein expression yields in CHO cells, and pharmacokinetic profile (for the most promising entity), leading to identification of a promising Fc(M3)-linker-CocH3 entity, as discussed below.

Materials and Methods

Materials

Q5® Site-Directed Mutagenesis Kit was ordered from New England Biolabs (Ipswich, Mass.). All oligonucleotides were synthesized by Eurofins MWG Operon (Huntsville, Ala.). Chinese Hamster Ovary-suspension (CHO-S) cells, FreeStyle™ CHO Expression Medium, Fetal Bovine Serum (FBS), 4-12% Tris-Glycine Mini Protein Gel, and SimpleBlue SafeStain were obtained from Invitrogen (Grand Island, N.Y.). TransIT-PRO® Transfection Kit was purchased from Minis (Madison, Wis.). The rmp Protein A Sepharose Fast Flow was from GE Healthcare Life Sciences (Pittsburgh, Pa.). (−)-Cocaine was provided by the National Institute on Drug Abuse (NIDA) Drug Supply Program (Bethesda, Md.); and [$^3$H](−)-Cocaine (50 Ci/mmol) was obtained from PerkinElmer (Waltham, Mass.). All other materials were from Sigma-Aldrich (St Louis, Mo.) or Thermo Fisher Scientific (Waltham, Mass.).

Preparation of Gene Fusion Constructs in pCMV-MCS

Q5® Site-Directed Mutagenesis Kit was used to introduce each linker between Fc(M3) and CocH3. The pCMV-Fc (M3)-CocH3, constructed in a previous study [32] to encode N-terminal Fc-fused CocH3 without a linker, was used as the template. PCR reactions with Q5 hot start high-fidelity DNA polymerase along with primers listed in Table 1 were utilized to create insertions. Then 1 µl of each PCR product was incubated with Kinase-Ligase-DpnI enzyme mix for 15 minutes at room temperature. These steps allowed for rapid circulation of the PCR product and removal of the template DNA. 5 µl of final product was added to 50 µl of chemically-competent *E. coli* cells for transformation. All obtained plasmid encoding different Fc-fused CocH3 were confirmed by DNA sequencing.

TABLE 1

Examples of primers for inserting various linkers

| Linker | Primer name | Primer sequence |
| --- | --- | --- |
| EAAAK | EAAAK-F | 5'-G TCT CCG GGT AAA GAG GCT GCC GCC AAG GAA GAT GAC ATC A-3' (SEQ ID NO: 20) |
|  | EAAAK-R | 5'-CTT GGC GGC AGC CTC TTT ACC CGG AGA CAG GGA GAG-3' (SEQ ID NO: 21) |
| PAPAP | PAPAP-F | 5'-G TCT CCG GGT AAA CCT GCT CCA GCC CCG GAA GAT GAC ATC A-3' (SEQ ID NO: 22) |
|  | PAPAP-R | 5'-CGG GGC TGG AGC AGG TTT ACC CGG AGA CAG GGA GAG-3' (SEQ ID NO: 23) |
| GGGSGGGS | $(G3S)_2$-F | 5'-G TCT CCG GGT AAA GGT GGA GGT TCC GGT GGA GGT TCC GAA GAT GAC ATC A-3' (SEQ ID NO: 24) |
|  | $(G3S)_2$-R | 5'- GGA ACC TCC ACC GGA ACC TCC ACC TTT ACC CGG AGA CAG GGA GAG-3' (SEQ ID NO: 25) |
| PAPAPPAPAP | $(PAPAP)_2$-F | 5'-G TCT CCG GGT AAA CCT GCT CCA GCC CCG CCT GCT CCA GCC CCG GAA GAT GAC ATC A-3' (SEQ ID NO: 26) |
|  | $(PAPAP)_2$-R | 5'- CGG GGC TGG AGC AGG CGG GGC TGG AGC AGG TTT ACC CGG AGA CAG GGA GAG-3' (SEQ ID NO: 27) |

Expression and Purification

CHO-S cells were grown under the condition of 37° C. and 8% $CO_2$ in a humidified atmosphere. Once cells grown to a density of ~1.0×10⁶ cells/ml, cells were transfected with plasmids encoding various proteins using TransIT-PRO® transfection kit. The culture medium was harvested 7 days after transfection. Enzyme secreted in the culture medium was purified by protein A affinity chromatography described previously [31]. Briefly, pre-equilibrated rmp Protein A Sepharose Fast Flow was mixed with cell-free medium, and incubated overnight at 6° C. with occasional stirring. Then the suspension was packed in a column, washed with 20 mM Tris.HCl (pH 7.4), and eluted by adjustment of salt concentration and pH. The eluate was concentrated and dialyzed in storage buffer (50 mM HEPES, 20% sorbitol, 1 M glycine, pH 7.4). Purified proteins were analyzed by native PAGE electrophoresis.

In Vitro Activity Assay Against (−)-Cocaine.

A radiometric assay based on toluene extraction of [³H] (−)-cocaine labeled on its benzene ring was used to determine the catalytic activity of proteins [9, 11, 33]. Reactions were initiated by adding 150 µl enzyme solution (100 mM phosphate buffer, pH 7.4) to 50 µl [³H](−)-cocaine solution with varying concentration. Then 200 µl of 0.1 M HCl was added to stop each reaction and neutralize the liberated benzoic acid while ensuring a positive charge on the residual (−)-cocaine. [³H]Benzoic acid was extracted by 1 ml of toluene and measured by scintillation counting. Catalytic rate constant ($k_{cat}$) and Michaelis-Menten constant ($K_m$) were determined by fitting the substrate concentration-dependent data using Michaelis-Menten kinetics.

Determination of Relative Expression Level of Proteins

Cells were grown in 12-well plates to a density of ~1.0×10⁶ cells/ml. Then cells were transfected with plasmids encoding different proteins using the same method described above. The test was tripled for each protein, occupying 3 out of 12 wells in a plate. Medium was collected from each well 3 days post the transfection. Cells were removed by centrifuge at 4000 rpm for 15 min, and the catalytic activity of each sample against cocaine was determined using radiometric assay described above. Protein concentration was calculated by dividing the catalytic activity by the $k_{cat}$ (determined by using the aforementioned purified protein) for each specific protein.

Determination of Biological Half-Life in Rats

Male Sprague-Darley rats (220-250 g) were ordered from Harlan (Harlan, Indianapolis, Ind.), and housed initially as one or two rats per cage. All rats were allowed ad libitum access to food and water and maintained on a 12 h light/12 h dark cycle, with the lights on at 8:00 a.m. at a room temperature of 21-22° C. Experiments were performed in a same colony room in accordance with the Guide for the Care and Use of Laboratory Animals as adopted and promulgated by the National Institutes of Health. The animal procedure was approved by the IACUC (Institutional Animal Care and Use Committee) as part of the animal protocol 2010-0722 on Jun. 21, 2016 at the University of Kentucky. Rats were injected with the purified Fc(M3)-$(PAPAP)_2$—CocH3 protein via tail vein (0.075 mg/kg). Blood samples were collected from saphenous vein puncture. Approximately 100 µl blood was collected by using heparin-treated capillary tube at various time points after enzyme administration. Collected samples were centrifuged for 15 min at a speed of 5000 g to separate the plasma, which was kept at 4° C. before analysis. Radiometric assay using 100 µM (−)-cocaine was carried out to measure the active enzyme concentration in plasma.

Results and Discussion

Optimization of Fc-Fused CocH3 Entity with a Linker

Four different linkers, including flexible linkers (GGGSGGGS) (SEQ ID NO: 6) (GGGGSGGGGS)(SEQ ID NO: 36), (GGGGGGSGGGGGGS)(SEQ ID NO: 37) and three rigid linkers (EAAAK—SEQ ID NO: 19), (PAPAP—SEQ ID NO: 4), and (PAPAPPAPAP-SEQ ID NO: 2), were utilized in this study. Previous studies reported in literature indicated that a linker similar to these could separate carrier protein and functional protein effectively and lead to improved biological activity of the fusion proteins with a linker. The four fusion proteins (see FIG. 1) with various linkers were then expressed, purified, and characterized for their catalytic activity against cocaine by performing the sensitive radiometric assay using [$^3$H](−)-cocaine with various concentrations. All of the fusion proteins have a size ~210 kDa (FIG. 2), which is consistent with the expected dimeric structure with disulfide bonds formed on the Fc part. CocH3, which was produced predominantly in a tetramer form in a previous study [9] has a $k_{cat}$ of 5700 min$^{-1}$; however, the fusion protein, Fc(M3)-CocH3, which was constructed without any linker in a previous study [32], exhibited only ~30% catalytic activity against cocaine as compared to the corresponding unfused CocH3.

To optimize the construct of Fc(M3)-CocH3, the above mentioned four linkers were used to eliminate the negative effects of N-terminal Fc portion on the catalytic activity of C-terminal CocH3. As seen in Table 2 and FIG. 3, with the insertion of a flexible linker $(G3S)_2$, CocH3(529)-$(G_3S)_2$-Fc(M3) [SEQ ID NO: 13-SEQ ID NO: 6-SEQ ID NO: 16] has a $k_{cat}$ of 3579 min$^{-1}$ which was 2-fold higher than that of the fusion protein without a linker. However, the $k_{cat}$ value of CocH3(529)-$(G_3S)_2$-Fc(M3) was still lower than that of the corresponding unfused CocH3 (SEQ ID NO: 13) (3579 min$^{-1}$ compared to 5700 min$^{-1}$). Nevertheless, Fc(M3)-EAAAK-CocH3[SEQ ID NO: 16-SEQ ID NO: 19-SEQ ID NO: 13], Fc(M3)-PAPAP-CocH3[SEQ ID NO: 16-SEQ ID NO: 4-SEQ ID NO: 13], and Fc(M3)-$(PAPAP)_2$-CocH3[SEQ ID NO: 16-SEQ ID NO: 2-SEQ ID NO: 13] all have a catalytic activity comparable to the $k_{cat}$ of the unfused CocH3. The $k_{cat}$ values of Fc(M3)-EAAAK-CocH3, Fc(M3)-PAPAP-CocH3, and Fc(M3)-$(PAPAP)_2$—CocH3 are 5287, 6078, and 5270 min$^{-1}$, respectively. As a rigid linker used in these fusion proteins provides enough space between the Fc(M3) and CocH3 domains, it is likely that these two protein domains can be fold correctly without affecting each other in terms of their functions, including the entrance to active site of CocH3 for cocaine. Further longer linker were not tested in this study for a couple of reasons. First, the currently designed linker could provide enough space for the two protein domains, thus fusing the Fc(M3) is not expected to affect the catalytic activity of CocH3 against cocaine. Further, a further longer linker between CocH3 and Fc could be proteolyzed easily and, thus, could shorten the biological half-life of the fusion protein [3].

TABLE 2

Kinetic parameters determined for (-)-cocaine hydrolysis catalysed by the fusion proteins

| Protein # | Enzyme | $K_m$ (μM) | $k_{cat}$ (min$^{-1}$) | $k_{cat}/K_M$ (min$^{-1}$ M$^{-1}$) |
|---|---|---|---|---|
| 1* | Fc(M3)CocH3(529) (SEQ ID NO: 16-SEQ ID NO: 13) | 3.9 ± 0.5 | 1835 ± 61 | $4.7 \times 10^8$ |
| 2* | Fc(M3)-$G_6$S-CocH3 (SEQ ID NO: 16-SEQ ID NO: 37-SEQ ID NO: 13) | 4.4 ± 0.6 | 5694 ± 238 | $1.3 \times 10^9$ |
| 3 | Fc(M3)-EAAAK-CocH3(529) (SEQ ID NO: 16-SEQ ID NO: 19-SEQ ID NO: 13) | 4.3 ± 0.4 | 5684 ± 148 | $1.3 \times 10^9$ |
| 4 | Fc(M3)-PAPAP-CocH3(529) (SEQ ID NO: 16-SEQ ID NO: 4-SEQ ID NO: 13) | 4.2 ± 0.5 | 6078 ± 202 | $1.4 \times 10^9$ |
| 5 | Fc(M3)-$(G_3S)_2$-CocH3(529) (SEQ ID NO: 16-SEQ ID NO: 6-SEQ ID NO: 6-SEQ ID NO: 13) | 3.7 ± 0.4 | 3579 ± 104 | $9.6 \times 10^8$ |
| 6 | Fc(M3)-$(PAPAP)_2$-CocH3(529) (SEQ ID NO: 16-SEQ ID NO: 2-SEQ ID NO: 13) | 4.5 ± 0.5 | 5666 ± 148 | $1.3 \times 10^9$ |

*The $k_{cat}$ and $K_M$ of the enzymes against (-)-cocaine were reported in ref. [32]

Effects of the Linker on the Expression of Fc(M3)-Fused CocH3 Protein

Fc(M3)-EAAAK-CocH3, Fc(M3)-PAPAP-CocH3, and Fc(M3)-$(PAPAP)_2$—CocH3 were further expressed together with Fc(M3)-CocH3 and the unfused CocH3 for comparison of relevant protein expression levels. All five proteins were expressed in the same plate under the same conditions at the same time. Cells in each well transfected using the same method and cultured under the same conditions after the transfection. All media were collected 3 days after the transfection. Protein expression level in each well was determined using the radiometric assay using 100 μM [$^3$H](−)-cocaine. As seen in Table 3, the expression of the unfused CocH3 was 0.5 mg/L 3 days after the transient transfection. Usually, inserting the Fc portion at the N-terminal of the target protein could significantly improve the protein expression level. In this study, directly fusing Fc to the N-terminal of CocH3 increased the protein expression level by ~2-fold. However, as Fc(M3)-CocH3 protein had only ~30% catalytic activity against cocaine as compared to the unfused CocH3 [32]. As Fc(M3) domain sterically interferes with the CocH3 domain activity and lowers its catalytic activity against cocaine, it is also possible that this steric interference affects the efficiency of the protein folding. Therefore, an appropriate linker capable of avoiding such steric interference may not only improve the catalytic activity against cocaine, but also increase the protein expression level. As shown in Table 3, the protein expression yields of Fc(M3)-EAAAK-CocH3 and Fc(M3)-PAPAP-CocH3 was 4.8, and 5.2 mg/L, respectively. Linkers EAAAK, and PAPAP improved the yield of Fc(M3)-CocH3 protein expression by ~9 and ~10 folds, respectively. Among all fusion proteins constructed in this study, Fc(M3)-(PAPAP)$_2$—CocH3 has the highest protein expression yield. The linker (PAPAPPAPAP) increased the yield of protein expression by ~10 fold compared to the corresponding fusion protein without a linker. Further, compared to the corresponding unfused protein (CocH3), Fc(M3)-(PAPAP)$_2$-CocH3 had a ~21-fold improved yield of protein expression.

Biological Half-Life of Fc(M3)-(PAPAP)$_2$—CocH3 in Rats

Figure 4:
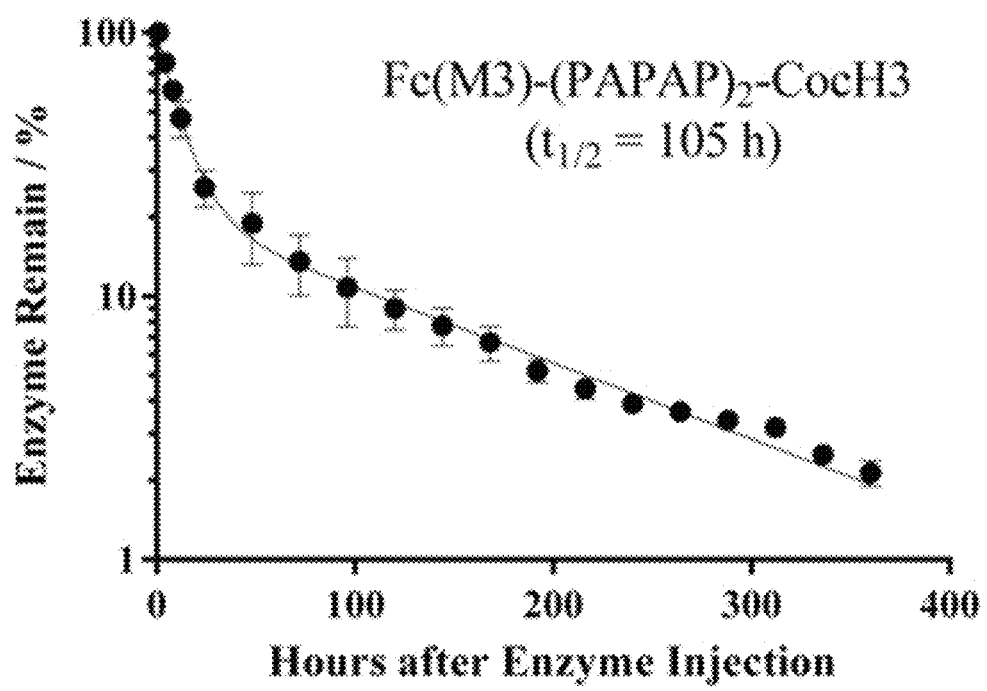
FIG. 4 is a graph illustrating the time-dependent concentration of Fc(M3)-(PAPAP)$_2$-CocH3 (SEQ ID NO: 16-SEQ ID NO: 2-SEQ ID NO: 15) fusion. in the plasma of rats after IV administration of the enzyme (0.075 mg/kg) determined in triplicate.
Figure 5:
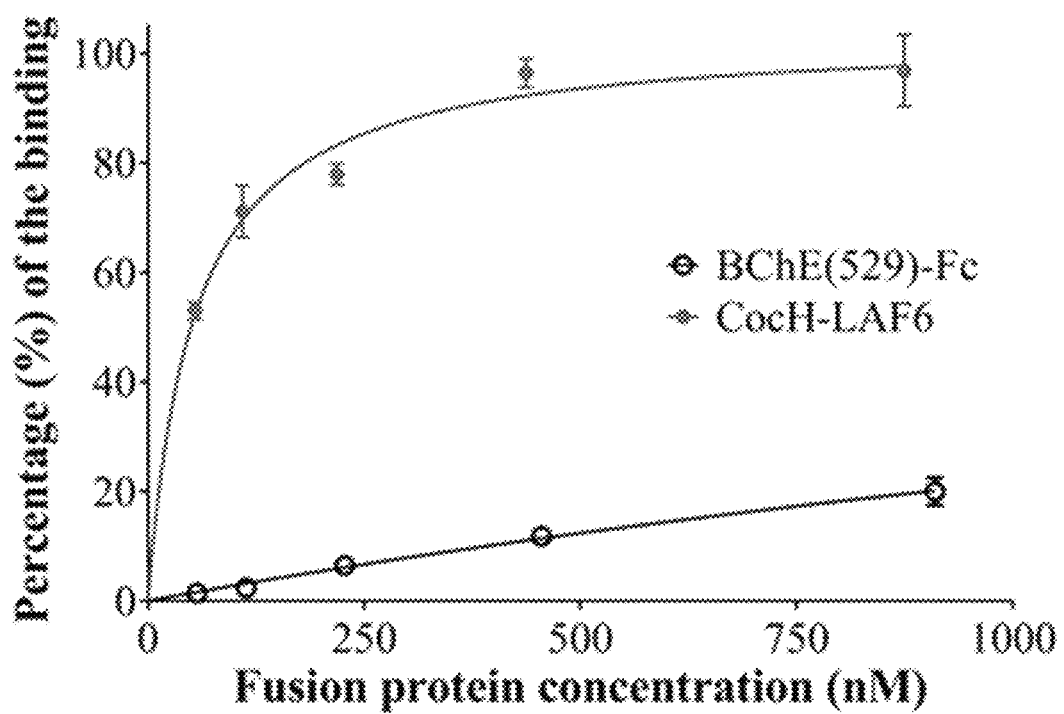
FIG. 5 shows Fc fusion protein CocH-LAF6 plots of the measured protein binding (%) vs the Fc-fused protein concentration.

Pharmacokinetic testing was carried out to determine biological half-life of Fc(M3)-(PAPAP)$_2$-CocH3. Rats (n=3) were administered IV with 0.075 mg/kg of the purified protein. The blood was collected at 1 hr, 4 hr, 8 hr, 12 hr, 1 day and once each day within 14 days after the enzyme injection. Depicted in FIG. 4 is the time course of the percentage of the enzyme activity remained after enzyme injection. The time-dependent data were fitted to a double-exponential equation ($[E]_t = Ae^{-k1t} + Be^{-k2t}$) by using the GraphPad Prism 6 software. For comparison, summarized in Table 4 are the biological half-lives (in mice/rats) of the native BChE (purified from human plasma) and recombinant BChE, BChE mutant, and CocH3-Fc(M3) produced using various methods. The biological half-life of Fc(M3)-(PAPAP)$_2$—CocH3 is ~105±7 hr, which is ~6.6-fold longer than the biological half-life of recombinant BChE or mutant produced using the same method, ~39-fold longer than the half-life of BChE produced in transgenic goat, and ~525-fold longer than the BChE mutant produced in transgenic plant. Even compared to native human BChE, Fc(M3)-(PAPAP)$_2$-CocH3 protein produced in CHO cells has a

TABLE 3

Transient expression levels of fusion proteins, in comparison of CocH3

| Enzyme | Expression level (mg/L) | Ratio |
|---|---|---|
| CocH3 (SEQ ID NO: 13) | 0.5 ± 0.1 | 1 |
| Fc(M3)-CocH3 (SEQ ID NO: 16-SEQ ID NO: 13) | 1.1 ± 0.2 | 2 |
| Fc(M3)-EAAAK-CocH3 (SEQ ID NO: 16-SEQ ID NO: 19-SEQ ID NO: 13) | 4.8 ± 0.6 | 9 |
| Fc(M3)-PAPAP-CocH3 (SEQ ID NO: 16-SEQ ID NO: 4-SEQ ID NO: 13) | 5.2 ± 0.6 | 10 |
| Fc(M3)-(PAPAP)$_2$-CocH3 (SEQ ID NO: 16-SEQ ID NO: 2-SEQ ID NO: 13) | 10.9 ± 1.1 | 21 |

It should be pointed out that the transient expression method (with the protein expression within only three days) in this study was used only for the purpose of comparing the relative expression levels of various fusion proteins and unfused protein under the same conditions. So, the key results of this study are the relative protein expression levels, rather than the absolute protein expression levels. The absolute protein expression levels are expected to significantly increase when the stable CHO cell lines are developed and used to express the same proteins; of course, development of a stable cell line is a very time-consuming process. For example, using a lentivirus-based repeated-transduction method which was established in a previous study [24], the protein expression yield of the unfused CocH3 reached ~10 mg/L in a flask-based culture. Thus, one would reasonably expect that an appropriately developed stable CHO cell line might be able to express ~200 mg/L Fc(M3)-(PAPAP)2-CocH3 protein by using the same lentivirus-based repeated-transduction method. The protein expression yield could be improved further by optimizing of the culture conditions, such as cell density, medium, and culture temperature.

~2.4-fold prolonged biological half-life. In a previously reported study [31], it was demonstrated that a novel CocH form, i.e. a C-terminal Fc-fused CocH3, known as CocH3-Fc(M3), had a biological half-life of ~107±6 hr in rats. But CocH3-Fc(M3) was expressed at a yield of ~2.1 mg/L in CHO cells under the similar conditions. The Fc(M3)-(PAPAP)$_2$—CocH3 reported in the current study has a similarly long half-life (105±7 hr vs 107±6 hr) compared to CocH3-Fc(M3) but with a significantly improved protein expression yield.

TABLE 4

Summary of biological half-life of BChE or mutants in mice or rats

| Protein form | In vivo half-life (h) |
|---|---|
| BChE purified from human plasma | 43[a] |
| BChE produced in transgenic goat | 2.7[b] |
| BChE mutant produced in transgenic plant | 0.2[c] |
| BChE mutant produced in CHO cells | 7.3[d] |

TABLE 4-continued

Summary of biological half-life of BChE or mutants in mice or rats

| Protein form | In vivo half-life (h) |
|---|---|
| CocH3-Fc(M3) produced in CHO cells (SEQ ID NO: 13-SEQ ID NO: 16) | 107[e] |
| Fc(M3)-(PAPAP)$_2$-CocH3 produced in CHO cells (SEQ ID NO: 16-SEQ ID NO: 2-SEQ ID NO: 13) | 105 |

[a]Biological half-life of enzyme was reported in ref. [26].
[b]Biological half-life of enzyme was reported in ref. [21].
[c]Biological half-life of enzyme was reported in ref. [19].
[d]Data from ref. [24].
[e]Data from ref. [31].

A previously reported study [31] demonstrated that a single injection of CocH-Fc(M3) was able to accelerate cocaine metabolism in rats after 20 days and, thus, block cocaine-induced physiological and toxic effects for a long period [31]. The CocH3-Fc(M3) protein was expected to allow dosing once every 2-4 wk, or longer, for treating cocaine addiction in humans. Given the facts that Fc(M3)-(PAPAP)$_2$-CocH3 has the similarly long biological half-life in rats and same catalytic activity against cocaine, it is reasonable to expect that Fc(M3)-(PAPAP)$_2$-CocH3 may also be able to provide the similar efficacy and duration for the cocaine addiction treatment.

It has been a significant challenge to efficiently express BChE polypeptides with both a long biological half-life comparable to the native BChE purified from human plasma and a high yield of protein expression. In this study, it has been demonstrated that an exemplary polypeptides including a BChE polypeptide molecule have not only a long biological half-life, but also an improved yield of protein expression compared to CocH3 (e.g., ~105±7 hr in rats and ~21-fold improved yield for Fc(M3)-(PAPAP)2-CocH3).

In a further example of the present invention:

BChE or BChE(574) refers to the wild-type human butyrylcholinesterase (full-length protein, with 574 amino acids) (SEQ ID NO:10). BChE(xxx) refers to a trucated fragment (with only the first xxx amino acids) of human butyrylcholinesterase (SEQ ID NO:10).

BChE-Fc refers to a fusion protein in which the C-terminus of human BChE (SEQ ID No: 10) is fused to the N-terminus of the Fc portion of human IgG-1 (SEQ ID NO: 8) or (SEQ ID NO 10-SEQ ID NO: 8). BChE(xxx)-Fc refers to a fusion protein in which the C-terminus of BChE(xxx) fragment fused to the N-terminus of the Fc portion of human IgG-1. CocH is a BChE polypeptide with specific mutations. CocH-LAF generally represents a cocaine hydrolase (CocH) in a long-acting form (LAF).

CocH-LAF1 (in which "1" means the first version) refers to the
(SEQ ID NO: 13-SEQ ID NO: 16)
A199S/F227A/S287G/A328W/Y332G/A530V/D671E/L673M mutant of BChE(529)-Fc.

CocH-LAF4 refers to the
(SEQ ID NO: 13-SEQ ID NO: 17)
A199S/F227A/S287G/A328W/Y332G/A530V/M567Y/D671E/L673M mutant of the BChE(529)-Fc protein.

CocH-LAF6 refers to the
((SEQ ID NO: 13-SEQ ID NO: 18)
A199S/F227A/S287G/A328W/Y332G/A530V/M567Y/S569T/T571E/D671E/L673M mutant of BChE(529)-Fc.

CocH-LAF7 refers to the
(SEQ ID NO: 14-SEQ ID NO: 18)
A199S/F227A/P285A/S287G/A328W/Y332G/A530V/M567Y/S569T/T571E/D671E/L673M mutant of BChE(529)-Fc.

CocH-LAF8 refers to the
(SEQ ID NO: 15-SEQ ID NO: 18)
A199S/F227A/P285Q/S287G/A328W/Y332G/A530V/M567Y/S569T/T571E/D671E/L673M mutant of BChE(529)-Fc.

TABLE 5

Transient expression levels of BChE-Fc and BChE(529)-Fc

| Protein | Expression level (mg/L) | Ratio |
|---|---|---|
| BChE-Fc (SEQ ID NO: 11-SEQ ID NO: 8) | 0.55 | 1 |
| BChE(529)-Fc (SEQ ID NO: 11-SEQ ID NO: 8) | 3.78 | 6.9 |

According to the data in Table 5, BChE(529)-Fc can be expressed with a significantly improved yield (about ~7 fold), compared BChE-Fc. Both the Fc fusion and BChE fragmentation did not significantly change the catalytic activity of BChE.

In light of the production data in Table 5, a further designed mutants of BChE(529)-Fc with an improved binding affinity with neonatal Fc receptor (FcRn) at pH 6 in order to further prolong the biological half-life ($t_{1/2}$) in addition to the protein expression yield (see Table S2).

TABLE 6

Binding affinity of BChE(529)-Fc and its mutants with human FcRn and their biological half-life ($t_{1/2}$), along with the protein expression levels in stably transfected CHO cells.

| Protein | $K_d$ (nM) with FcRn at pH 6 | $t_{1/2}$ (hours) in rats | Expression level[a] |
|---|---|---|---|
| BChE(529)-Fc (SEQ ID NO: 11-SEQ ID NO: 8) | 2500 to 4000 | 86 ± 6 | >100 mg/L |
| CocH3-LAF1 (SEQ ID NO: 13-SEQ ID NO: 16) | 992 | 107 ± 6 | >1 g/L |
| CocH3-LAF4 (SEQ ID NO: 13-SEQ ID NO: 17) | 327 | 195 ± 10 | >1 g/L |
| CocH3-LAF6 (SEQ ID NO: 13-SEQ ID NO: 18) | 43 | 206 ± 7 | >200 mg/L |

TABLE 6-continued

Binding affinity of BChE(529)-Fc and its mutants with human FcRn and their biological half-life ($t_{1/2}$), along with the protein expression levels in stably transfected CHO cells.

| Protein | $K_d$ (nM) with FcRn at pH 6 | $t_{1/2}$ (hours) in rats | Expression level[a] |
|---|---|---|---|
| CocH1-LAF7 (SEQ ID NO: 14-SEQ ID NO: 18) | 43 | 206 ± 7 | >1 g/L |
| CocH2-LAF8 (SEQ ID NO: 15-SEQ ID NO: 18) | 43 | 206 ± 7 | >200 mg/L |

[a]The protein expression level is also affected by the culture conditions. Listed here is the lower end of the protein expression level.

To illustrate the approach to the rational design and discovery of BChE(529)-Fc mutants with improved binding affinity with FcRn and prolonged biological half-lives, depicted in FIG. 5 is the in vitro data for the binding affinity of CocH-LAF6.

CocH3 represents the A199S/F227A/S287G/A328W/Y332G mutant of human butyrylcholinesterase (BChE). The full-length BChE or CocH3 has 574 amino-acid residues. CocH3(xxx) refers to the fragment (with only the first xxx amino acids) of the A199S/F227A/S287G/A328W/Y332G mutant of human butyrylcholinesterase.

TABLE 7

Transient expression levels of fusion proteins

| Enzyme | Expression level (mg/L) |
|---|---|
| CocH3(574) (SEQ ID NO: 12) | 0.51 |
| Fc(M3)-CocH3(529) (SEQ ID NO: 16-SEQ ID NO: 13) | 1.05 |
| Fc(M3)-$G_3$S-CocH3(529) (SEQ ID NO: 16-SEQ ID NO: 6-SEQ ID NO: 13) | 3.10 |
| Fc(M3)-$G_4$S-CocH3(529) (SEQ ID NO: 16-SEQ ID NO: 36-SEQ ID NO: 13) | 3.69 |
| Fc(M3)-$G_6$S-CocH3(529) (SEQ ID NO: 16-SEQ ID NO: 37-SEQ ID NO: 13) | 5.14 |
| Fc(M3)-EAAAK-CocH3(529) (SEQ ID NO: 16-SEQ ID NO: 19-SEQ ID NO: 13) | 4.76 |
| Fc(M3)-PAPAP-CocH3(529) (SEQ ID NO: 16-SEQ ID NO: 4-SEQ ID NO: 13) | 5.15 |

TABLE 7-continued

Transient expression levels of fusion proteins

| Enzyme | Expression level (mg/L) |
|---|---|
| CocH3(529)-$(G_3S)_2$-Fc(M3) (SEQ ID NO: 13-SEQ ID NO: 6-SEQ ID NO: 6-SEQ ID NO: 16) | 7.86 |
| Fc(M3)-$(PAPAP)_2$-CocH3(529) (SEQ ID NO: 16-SEQ ID NO: 2-SEQ ID NO: 13) | 10.87 |
| CocH3(574)-Fc(M3) (SEQ ID NO: 12-SEQ ID NO: 16) | 4.11 |
| CocH3(574)-$G_6$S-Fc(M3) (SEQ ID NO: 12-SEQ ID NO: 37-SEQ ID NO: 16) | 3.96 |
| CocH3(529)-Fc(M3) (SEQ ID NO: 13-SEQ ID NO: 16) | 5.75 |
| CocH3(529)-$G_6$S-Fc(M3) (SEQ ID NO: 13-SEQ ID NO: 37-SEQ ID NO: 16) | 6.39 |
| CocH3(529)-Fc(M6) (SEQ ID NO: 13-SEQ ID NO: 18) | 3.89 |

It will be understood that various details of the presently disclosed subject matter can be changed without departing from the scope of the subject matter disclosed herein. Furthermore, the foregoing description is for the purpose of illustration only, and not for the purpose of limitation.

All publications, patents, and patent applications mentioned in this specification are herein incorporated by reference to the same extent as if each individual publication, patent, or patent application was specifically and individually indicated to be incorporated by reference, including the references set forth in the following list:

SEQUENCE LISTING

SEQ ID NO: 1 Nucleotide Encoding SEQ ID NO: 2
CCGGCGCCGGCGCCGCCGGCGCCGGCGCCG

SEQ ID NO: 2
PAPAPPAPAP

SEQ ID NO: 3 Nucleotide encoding SEQ ID NO: 4
CCGGCGCCGGCGCCG

SEQ ID NO: 4
PAPAP

SEQUENCE LISTING

SEQ ID NO: 5 Nucleotide encoding SEQ ID NO: 6
GGCGGCGGCAGCGGCGGCGGCAGC

SEQ ID NO: 6
GGGSGGGS

SEQ ID NO: 7-Nucleotide encoding Wild type Fc polypeptide
GCA GAG CCT AAG TCC TGC GAC AAA ACT CAC ACA TGC CCA CCG TGC CCA
GCA CCT GAA CTC CTG GGG GGA CCG TCA GTC TTC CTC TTC CCC CCA AAA CCC
AAG GAC ACC CTC ATG ATC TCC CGG ACC CCT GAG GTC ACA TGC GTG GTG GTG
GAC GTG AGC CAC GAA GAC CCT GAG GTC AAG TTC AAC TGG TAC GTG GAC
GGC GTG GAG GTG CAT AAT GCC AAG ACA AAG CCG CGG GAG GAG CAG TAC
AAC AGC ACG TAC CGT GTG GTC AGC GTC CTC ACC GTC CTG CAC CAG GAC TGG
CTG AAT GGC AAG GAG TAC AAG TGC AAG GTC TCC AAC AAA GCC CTC CCA
GCC CCC ATC GAG AAA ACC ATC TCC AAA GCC AAA GGG CAG CCC CGA GAA
CCA CAG GTG TAC ACC CTG CCC CCA TCC CGG GAC GAG CTG ACC AAG AAC
CAG GTC AGC CTG ACC TGC CTG GTC AAA GGC TTC TAT CCC AGC GAC ATC GCC
GTG GAG TGG GAG AGC AAT GGG CAG CCG GAG AAC AAC TAC AAG ACC ACG
CCT CCC GTG CTG GAC TCC GAC GGC TCC TTC TTC CTC TAC AGC AAG CTC ACC
GTG GAC AAG AGC AGG TGG CAG CAG GGG AAC GTC TTC TCA TGC TCC GTG
ATG CAC GAG GCT CTG CAC AAC CAC TAC ACG CAG AAG AGC CTC TCC CTG TCT
CCG GGT AAA SEQ ID NO: 8-Wild type Fc polypeptide
AEPKSCDKTH TCPPCPAPEL LGGPSVFLFP PKPKDTLMIS RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS RDELTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 9-Nucleotide encoding Wild type BChE
GAA GAT GAC ATC ATA ATT GCA ACA AAG AAT GGA AAA GTC AGA GGG ATG
AAC TTG ACA GTT TTT GGT GGC ACG GTA ACA GCC TTT CTT GGA ATT CCC TAT
GCA CAG CCA CCT CTT GGT AGA CTT CGA TTC AAA AAG CCA CAG TCT CTG ACC
AAG TGG TCT GAT ATT TGG AAT GCC ACA AAA TAT GCA AAT TCT TGC TGT CAG
AAC ATA GAT CAA AGT TTT CCA GGC TTC CAT GGA TCA GAG ATG TGG AAC CCA
AAC ACT GAC CTC AGT GAA GAC TGT TTA TAT CTA AAT GTA TGG ATT CCA GCA
CCT AAA CCA AAA AAT GCC ACT GTA TTG ATA TGG ATT TAT GGT GGT GGT TTT
CAA ACT GGA ACA TCA TCT TTA CAT GTT TAT GAT GGC AAG TTT CTG GCT CGG
GTT GAA AGA GTT ATT GTA GTG TCA ATG AAC TAT AGG GTG GGT GCC CTA GGA
TTC TTA GCT TTG CCA GGA AAT CCT GAG GCT CCA GGG AAC ATG GGT TTA TTT
GAT CAA CAG TTG GCT CTT CAG TGG GTT CAA AAA AAT ATA GCA GCC TTT GGT
GGA AAT CCT AAA AGT GTA ACT CTC TTT GGA GAA AGT GCA GGA GCA GCT TCA
GTT AGC CTG CAT TTG CTT TCT CCT GGA AGC CAT TCA TTG TTC ACC AGA GCC
ATT CTG CAA AGT GGT TCC TTT AAT GCT CCT TGG GCG GTA ACA TCT CTT TAT
GAA GCT AGG
AAC AGA ACG TTG AAC TTA GCT AAA TTG ACT GGT TGC TCT AGA GAG AAT GAG
ACT AGA ATA ATC AAG TGT CTT AGA AAT AAA GAT CCC CAA GCA ATT CTT CTG
AAT GAA GCA TTT GTT GTC CCC TAT GGG ACT CCT TTG TCA GTA AAC TTT GGT
CCG ACC GTG GAT GGT GAT TTT CTC ACT GAC ATG CCA GAC ATA TTA CTT GAA
CTT GGA CAA TTT AAA AAA ACC CAG ATT TTG GTG GGT GTT AAT AAA GAT GAA
GGG ACA GCT TTT TTA GTC TAT GGT GCT CCT GGC TTC AGC AAA GAT AAC AAT
AGT ATC ATA ACT AGA AAA GAA TTT CAG GAA GGT TTA AAA ATA TTT TTT CCA
GGA GTG AGT GAG TTT GGA AAG GAA TCC ATC CTT TTT CAT TAC ACA GAC TGG
GTA GAT GAT CAG AGA CCT GAA AAC TAC CGT GAG GCC TTG GGT GAT GTT GTT
GGG GAT TAT AAT TTC ATA TGC CCT GCC TTG GAG TTC ACC AAG AAG TTC TCA
GAA TGG GGA AAT AAT GCC TTT TTC TAC TAT TTT GAA CAC CGA TCC TCC AAA
CTT CCG TGG CCA GAA TGG ATG GGA GTG ATG CAT GGC TAT GAA ATT GAA TTT
GTC TTT GGT TTA CCT CTG GAA AGA AGA GAT AAT TAC ACA AAA GCC GAG
GAA ATT TTG AGT AGA TCC ATA GTG AAA CGG TGG GCA AAT TTT GCA AAA TAT
GGG AAT CCA
AAT GAG ACT CAG AAC AAT AGC ACA AGC TGG CCT GTC TTC AAA AGC ACT
GAA CAA AAA TAT CTA ACC TTG AAT ACA GAG TCA ACA AGA ATA ATG ACG
AAA CTA CGT GCT CAA CAA TGT CGA TTC TGG ACA TCA TTT TTT CCA AAA GTC
TTG GAA ATG ACA GGA AAT ATT GAT GAA GCA GAA TGG GAG TGG AAA GCA
GGA TTC CAT CGC TGG AAC AAT TAC ATG ATG GAC TGG AAA AAT CAA TTT AAC
GAT TAC ACT AGC AAG AAA GAA AGT TGT GTG GGT CTC SEQ ID NO: 10-Wild type BChE Polypeptide
EDDIIIATKNGKVRGMNLTVFGGTVTAFLGIPYAQPPLGRLRFKKPQSLTKWSDIWNATK
YANSCCQNIDQSFPGFHGSEMWNPNTDLSEDCLYLNVWIPAPKPKNATVLIWIYGGGFQ
TGTSSLHVYDGKFLARVERVIVVSMNYRVGALGFLALPGNPEAPGNMGLFDQQLALQ
WVQKNIAAFGGNPKSVTLFGESAGAASVSLHLLSPGSHSLFTRAILQSGSFNAPWAVTSL
YEARNRTLNLAKLTGCSRENETEIIKCLRNKDPQEILLNEAFVVPYGTPLSVNFGPTVDG
DFLTDMPDILLELGQFKKTQILVGVNKDEGTAFLVYGAPGFSKDNNSIITRKEFQEGLKIF
FPGVSEFGKESILFHYTDWVDDQRPENYREALGDVVGDYNFICPALEFTKKFSEWGNNA FFYYFERRSSKLPWPEWMGVMHGYEIEFVFGLPLERRDNYTKAEEILSRSIVKRWANFA
KYGNPNETQNNSTSWPVFKSTEQKYLTLNTESTRIMTKLRAQQCRFWTSFFPKVLEMTG
NIDEAEWEWKAGFHRWNNYMMDWKNQFNDYTSKKESCVGL SEQ ID NO: 11-Truncated (only the first 529 amino acids of wild type BChE)
BchE (529)
EDDIIIATKNGKVRGMNLTVFGGTVTAFLGIPYAQPPLGRLRFKKPQSLTKWSDIWNATK
YANSCCQNIDQSFPGFHGSEMWNPNTDLSEDCLYLNVWIPAPKPKNATVLIWIYGGGFQ
TGTSSLHVYDGKFLARVERVIVVSMNYRVGALGFLALPGNPEAPGNMGLFDQQLALQ
WVQKNIAAFGGNPKSVTLFGESAGAASVSLHLLSPGSHSLFTRAILQSGSFNAPWAVTSL
YEARNRTLNLAKLTGCSRENETEIIKCLRNKDPQEILLNEAFVVPYGTPLSVNFGPTVDG
DFLTDMPDILLELGQFKKTQILVGVNKDEGTAFLVYGAPGFSKDNNSIITRKEFQEGLKIF
FPGVSEFGKESILFHYTDWVDDQRPENYREALGDVVGDYNFICPALEFTKKFSEWGNNA
FFYYFERRSSKLPWPEWMGVMHGYEIEFVFGLPLERRDNYTKAEEILSRSIVKRWANFA
KYGNPNETQNNSTSWPVFKSTEQKYLTLNTESTRIMTKLRAQQCRFWTSFFPKV SEQ ID NO: 12-CoCH3 Full length (574)
EDDIIIATKNGKVRGMNLTVFGGTVTAFLGIPYAQPPLGRLRFKKPQSLTKWSDIWNATK
YANSCCQNIDQSFPGFHGSEMWNPNTDLSEDCLYLNVWIPAPKPKNATVLIWIYGGGFQ
TGTSSLHVYDGKFLARVERVIVVSMNYRVGALGFLALPGNPEAPGNMGLFDQQLALQ
WVQKNIAAFGGNPKSVTLFGESSGAASVSLHLLSPGSHSLFTRAILQSGSANAPWAVTSL
YEARNRTLNLAKLTGCSRENETEIIKCLRNKDPQEILLNEAFVVPYGTPLGVNFGPTVDG
DFLTDMPDILLELGQFKKTQILVGVNKDEGTWFLVGGAPGFSKDNNSIITRKEFQEGLKI
FFPGVSEFGKESILFHYTDWVDDQRPENYREALGDVVGDYNFICPALEFTKKFSEWGNN
AFFYYFEHRSSKLPWPEWMGVMHGYEIEFVFGLPLERRDNYTKAEEILSRSIVKRWANF
AKYGNPNETQNNSTSWPVFKSTEQKYLTLNTESTRIMTKLRAQQCRFWTSFFPKVLEMT
GNIDEAEWEWKAGFHRWNNYMMDWKNQFNDYTSKKESCVGL SEQ ID NO: 13-Truncated CoCH3 (only the first 529 amino acids of Full length
CoCH3)(529)
EDDIIIATKNGKVRGMNLTVFGGTVTAFLGIPYAQPPLGRLRFKKPQSLTKWSDIWNATK
YANSCCQNIDQSFPGFHGSEMWNPNTDLSEDCLYLNVWIPAPKPKNATVLIWIYGGGFQ
TGTSSLHVYDGKFLARVERVIVVSMNYRVGALGFLALPGNPEAPGNMGLFDQQLALQ
WVQKNIAAFGGNPKSVTLFGESSGAASVSLHLLSPGSHSLFTRAILQSGSANAPWAVTSL
YEARNRTLNLAKLTGCSRENETEIIKCLRNKDPQEILLNEAFVVPYGTPLGVNFGPTVDG
DFLTDMPDILLELGQFKKTQILVGVNKDEGTWFLVGGAPGFSKDNNSIITRKEFQEGLKI
FFPGVSEFGKESILFHYTDWVDDQRPENYREALGDVVGDYNFICPALEFTKKFSEWGNN
AFFYYFEHRSSKLPWPEWMGVMHGYEIEFVFGLPLERRDNYTKAEEILSRSIVKRWANF
AKYGNPNETQNNSTSWPVFKSTEQKYLTLNTESTRIMTKLRAQQCRFWTSFFPKV SEQ ID NO: 14-CoCH1
EDDIIIATKNGKVRGMNLTVFGGTVTAFLGIPYAQPPLGRLRFKKPQSLTKWSDIWNATK
YANSCCQNIDQSFPGFHGSEMWNPNTDLSEDCLYLNVWIPAPKPKNATVLIWIYGGGFQ
TGTSSLHVYDGKFLARVERVIVVSMNYRVGALGFLALPGNPEAPGNMGLFDQQLALQ
WVQKNIAAFGGNPKSVTLFGESSGAASVSLHLLSPGSHSLFTRAILQSGSANAPWAVTSL
YEARNRTLNLAKLTGCSRENETEIIKCLRNKDPQEILLNEAFVVPYGTALGVNFGPTVDG
DFLTDMPDILLELGQFKKTQILVGVNKDEGTWFLVGGAPGFSKDNNSIITRKEFQEGLKI
FFPGVSEFGKESILFHYTDWVDDQRPENYREALGDVVGDYNFICPALEFTKKFSEWGNN
AFFYYFEHRSSKLPWPEWMGVMHGYEIEFVFGLPLERRDNYTKAEEILSRSIVKRWANF
AKYGNPNETQNNSTSWPVFKSTEQKYLTLNTESTRIMTKLRAQQCRFWTSFFPKV SEQ ID NO: 15-CoCH2
EDDIIIATKNGKVRGMNLTVFGGTVTAFLGIPYAQPPLGRLRFKKPQSLTKWSDIWNATK
YANSCCQNIDQSFPGFHGSEMWNPNTDLSEDCLYLNVWIPAPKPKNATVLIWIYGGGFQ
TGTSSLHVYDGKFLARVERVIVVSMNYRVGALGFLALPGNPEAPGNMGLFDQQLALQ
WVQKNIAAFGGNPKSVTLFGESSGAASVSLHLLSPGSHSLFTRAILQSGSANAPWAVTSL
YEARNRTLNLAKLTGCSRENETEIIKCLRNKDPQEILLNEAFVVPYGTQLGVNFGPTVDG
DFLTDMPDILLELGQFKKTQILVGVNKDEGTWFLVGGAPGFSKDNNSIITRKEFQEGLKI
FFPGVSEFGKESILFHYTDWVDDQRPENYREALGDVVGDYNFICPALEFTKKFSEWGNN
AFFYYFEHRSSKLPWPEWMGVMHGYEIEFVFGLPLERRDNYTKAEEILSRSIVKRWANF
AKYGNPNETQNNSTSWPVFKSTEQKYLTLNTESTRIMTKLRAQQCRFWTSFFPKV SEQ ID NO: 16-Fc(M3)
VEPKSCDKTH TCPPCPAPEL LGGPSVFLFP PKPKDTLMIS RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS REEMTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 17-Fc(M4)
VEPKSCDKTH TCPPCPAPEL LGGPSVFLFP PKPKDTYIS RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS REEMTKNQVS
LTCLVKGFYP SDIAVEWESN GQPENNYKTT PPVLDSDGSF FLYSKLTVDK
SRWQQGNVFS CSVMHEALHN HYTQKSLSLS PGK

SEQUENCE LISTING

```
SEQ ID NO: 18-Fc(M6)
VEPKSCDKTH TCPPCPAPEL LGGPSVFLFP PKPKDTYIT REPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS REEMTKNQVS
LTCLVKGFYP SDIAVEWESN GQPENNYKTT PPVLDSDGSF FLYSKLTVDK
SRWQQGNVFS CSVMHEALHN HYTQKSLSLS PGK

SEQ ID NO: 19-EAAAK Polypeptide
EAAAK

SEQ ID NO: 20-EAAAK-Forward Primer
G TCT CCG GGT AAA GAG GCT GCC GCC AAG GAA GAT GAC ATC A SEQ ID NO: 21-EAAAK-Reverse Primer
CTT GGC GGC AGC CTC TTT ACC GGA AGA CAG GGA GAG SEQ ID NO: 22-PAPAP-Forward Primer
G TCT CCG GGT AAA CCT GCT CCA GCC CCG GAA GAT GAC ATC SEQ ID NO: 23-PAPAP-Reverse Primer
CGG GGC TGG AGC AGG TTT ACC GGA AGA CAG GGA GAG SEQ ID NO: 24-(G3S)2-Forward Primer
G TCT CCG GGT AAA GGT GGA GGT TCC GGT GGA GGT TCC GAA GAT GAC ATC A SEQ ID NO: 25-(G3S)2-Reverse Primer
GGA ACC TCC ACC GGA ACC TCC ACC TTT ACC GGA AGA CAG GGA GAG SEQ ID NO: 26-(PAPAP)2-Forward Primer
G TCT CCG GGT AAA CCT GCT CCA GCC CCG CCT GCT CCA GCC CCG GAA GAT
GAC ATC SEQ ID NO: 27-(PAPAP)2-Reverse Primer
CGG GGC TGG AGC AGG CGG GGC TGG AGC AGG TTT ACC GGA AGA CAG GGA
GAG SEQ ID NO: 28-Fc(M8)
VEPKSCDKTH TCPPCPAPEL LGGPSVFLFP PKPKDTLMIS RTPEVTCVVV
DVSHEDPQVK FNWYVDGVQV HNAKTKPREQ QYNSTYRVVS VLTVLHQNWL
DGKEYKCKVS NKALPAPIEK TISKAKGQPR EPQVYTLPPS REEMTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 29-Fc(M5)
QEPKSSDKTH TSPPSPAPEL LGGSSVFLFP PKPKDTLMIS RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS RDELTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 30-Fc(M4')
VEPKSCDKTH TCPPCPAPEL LGGPSVFLFP PKPKDTLMIS REPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS REEMTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 31-Fc(M5')
VEPKSCDKTH TCPPCPAPEL LGGPSVFLFP PKPKDTLYIT RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS REEMTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 32-Fc(M6')
QEPKSSDKTH TSPPSPAPEL LGGSSVFLFP PKPKDTLYIS RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS RDELTKNQVS
LTCLVKGFYP SDIAVEWESN GQPENNYKTT PPVLDSDGSF FLYSKLTVDK
SRWQQGNVFS CSVMHEALHN HYTQKSLSLS PGK SEQ ID NO: 33-Fc(M7)
QEPKSSDKTH TSPPSPAPEL LGGSSVFLFP PKPKDTLYIT RTPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS RDELTKNQVS
```

```
                    SEQUENCE LISTING

LTCLVKGFYP SDIAVEWESN GQPENNYKTT PPVLDSDGSF FLYSKLTVDK
SRWQQGNVFS CSVMHEALHN HYTQKSLSLS PGK

SEQ ID NO: 34-Fc(M8')
QEPKSSDKTH TSPPSPAPEL LGGSSVFLFP PKPKDTLYIT REPEVTCVVV
DVSHEDPEVK FNWYVDGVEV HNAKTKPREE QYNSTYRVVS VLTVLHQDWL
NGKEYKCKVS NKALPAPIEK TISKAKGQPR EPQVYTLPPS RDELTKNQVS
LTCLVKGFYP SDIAVEWESN GQPENNYKTT PPVLDSDGSF FLYSKLTVDK
SRWQQGNVFS CSVMHEALHN HYTQKSLSLS PGK

SEQ ID NO: 35-wild type Fc-Truncated wild type BChE-fusion polypeptide
AEPKSCDKTH TCPPCPAPEL LGGPSVFLFP PKPKDTLMIS
RTPEVTCVVVDVSHEDPEVK FNWYVDGVEV HNAKTKPREE QYNSTYRVVS
VLTVLHQDWL NGKEYKCKVS NKALPAPIEK TISKAKGQPR EPQVYTLPPS
RDELTKNQVS LTCLVKGFYP SDIAVEWESN GQPENNYKTT PPVLDSDGSF
FLYSKLTVDK SRWQQGNVFS CSVMHEALHN HYTQKSLSLS
PGKEDDIIIATKNGKVRGMNLTVFGGTVTAFLGIPYAQPPLGRLRFKKPQSLTKWSDIWN
ATKYANSCCQNIDQSFPGFHGSEMWNPNTDLSEDCLYLNVWIPAPKPKNATVLIWIYGG
GFQTGTSSLHVYDGKFLARVERVIVVSMNYRVGALGFLALPGNPEAPGNMGLFDQQLA
LQWVQKNIAAFGGNPKSVTLFGESAGAASVSLHLLSPGSHSLFTRAILQSGSFNAPWAV
TSLYEARNRTLNLAKLTGCSRENETEIIKCLRNKDPQEILLNEAFVVPYGTPLSVNFGPTV
DGDFLTDMPDILLELGQFKKTQILVGVNKDEGTAFLVYGAPGFSKDNNSIITRKEFQEGL
KIFFPGVSEFGKESILPHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWA
NFAKYGNPNETQNNSTSWPVFKSTEQKYLTLNTESTRIMTKLRAQQCRFWTSFFPKV

SEQ ID NO: 36-G₄S
GGGGS GGGGS

SEQ ID NO: 37-G₆S
GGGGGGS GGGGGGS
```

REFERENCES

[1] O. Lockridge, Review of human butyrylcholinesterase structure, function, genetic variants, history of use in the clinic, and potential therapeutic uses, Pharmacol Ther, 148 (2015) 34-46.

[2] D. Cerasoli, E. Griffiths, B. Doctor, A. Saxena, J. Fedorko, N. Greig, Q. Yu, Y. Huang, H. Wilgus, C. Karatzas, (07) In vitro and in vivo characterization of recombinant human butyrylcholinesterase (Protexia™) as a potential nerve agent bioscavenger, Chemico-biological interactions, 157 (2005) 362-365.

[3] D. E. Lenz, D. Yeung, J. R. Smith, R. E. Sweeney, L. A. Lumley, D. M. Cerasoli, Stoichiometric and catalytic scavengers as protection against nerve agent toxicity: a mini review, Toxicology, 233 (2007) 31-39.

[4] Y. Ashani, S. Shapira, D. Levy, A. D. Wolfe, B. P. Doctor, Butyrylcholinesterase and acetylcholinesterase prophylaxis against soman poisoning in mice, Biochem Pharmacol, 41 (1991) 37-41.

[5] R. Brandeis, L. Raveh, J. Grunwald, E. Cohen, Y. Ashani, Prevention of soman-induced cognitive deficits by pretreatment with human butyrylcholinesterase in rats, Pharmacology Biochemistry and Behavior, 46 (1993) 889-896.

[6] N. Allon, L. Raveh, E. Gilat, E. Cohen, J. Grunwald, Y. Ashani, Prophylaxis against soman inhalation toxicity in guinea pigs by pretreatment alone with human serum butyrylcholinesterase, Toxicol Sci, 43 (1998) 121-128.

[7] H. Sun, Y.-P. Pang, O. Lockridge, S. Brimijoin, Re-engineering Butyrylcholinesterase as a Cocaine Hydrolase, Mol Pharmacol, 62 (2002) 220-224.

[8] S. Brimijoin, Y. Gao, J. J. Anker, L. A. Gliddon, D. LaFleur, R. Shah, Q. Zhao, M. Singh, M. E. Carroll, A Cocaine Hydrolase Engineered from Human Butyrylcholinesterase Selectively Blocks Cocaine Toxicity and Reinstatement of Drug Seeking in Rats, Neuropsychopharmacology, 33 (2008) 2715-2725.

[9] F. Zheng, W. C. Yang, M. C. Ko, J. J. Liu, H. Cho, D. Q. Gao, M. Tong, H. H. Tai, J. H. Woods, C.-G. Zhan, Most Efficient Cocaine Hydrolase Designed by Virtual Screening of Transition States, J Am Chem Soc, 130 (2008) 12148-12155.

[10] L. Xue, M.-C. Ko, M. Tong, W. Yang, S. Hou, L. Fang, J. Liu, F. Zheng, J. H. Woods, H.-H. Tai, C.-G. Zhan, Design, preparation, and characterization of high-activity mutants of human butyrylcholinesterase specific for detoxification of cocaine, Mol Pharmacol, 79 (2011) 290-297.

[11] L. Fang, F. Zheng, C.-G. Zhan, A model of glycosylated human butyrylcholinesterase, Mol. BioSyst., 10 (2014) 348-354.

[12] Y. Pan, D. Gao, W. Yang, H. Cho, G. Yang, H.-H. Tai, C.-G. Zhan, Computational redesign of human butyrylcholinesterase for anticocaine medication, Proc Natl Acad Sci USA, 102 (2005) 16656-16661.

[13] O. Cohen-Barak, J. Wildeman, J. van de Wetering, J. Hettinga, P. Schuilenga-Hut, A. Gross, S. Clark, M. Bassan, Y. Gilgun-Sherki, B. Mendzelevski, O. Spiegelstein, Safety, Pharmacokinetics, and Pharmacodynamics of TV-1380, a Novel Mutated Butyrylcholinesterase Treatment for Cocaine Addiction, After Single and Multiple Intramuscular Injections in Healthy Subjects, J Clin Pharmacol, 55 (2015) 573-583.

[14] M. J. Shram, O. Cohen-Barak, B. Chakraborty, M. Bassan, K. A. Schoedel, H. Hallak, E. Eyal, S. Weiss, Y. Gilgun, E. M. Sellers, J. Faulknor, O. Spiegelstein, Assessment of Pharmacokinetic and Pharmacodynamic Interactions Between Albumin-Fused Mutated Butyrylcholinesterase and Intravenously Administered Cocaine in Recreational Cocaine Users, J Clin Psychopharmacol, 35 (2015) 396-405.

[15] F. Zheng, C.-G. Zhan, Are pharmacokinetic approaches feasible for treatment of cocaine addiction and overdose?, Future Med Chem, 4 (2012) 125-128.

[16] P. Masson, A. Steve, P.-t. Philippe, L. Oksana, Multidisciplinary approaches to cholinesterase functions. expression and refoldin of functional human butyrylcholinesterase in, E. coli.

[17] W.-L. Wei, J.-C. Qin, M.-J. Sun, High-level expression of human butyrylcholinesterase gene in Bombyx mori and biochemical-pharmacological characteristic study of its product, Biochemical pharmacology, 60 (2000) 121-126.

[18] X. Brazzolotto, M. Wandhammer, C. Ronco, M. Trovaslet, L. Jean, O. Lockridge, P. Y. Renard, F. Nachon, Human butyrylcholinesterase produced in insect cells: huprine-based affinity purification and crystal structure, FEBS Journal, 279 (2012) 2905-2916.

[19] G. Wang, T. Zhang, H. Huang, S. Hou, X. Chen, F. Zheng, C.-G. Zhan, Plant expression of cocaine hydrolase-Fc fusion protein for treatment of cocaine abuse, BMC biotechnology, 16 (2016) 72.

[20] B. C. Geyer, L. Kannan, I. Cherni, R. R. Woods, H. Soreq, T. S. Mor, Transgenic plants as a source for the bioscavenging enzyme, human butyrylcholinesterase, Plant biotechnology journal, 8 (2010) 873-886.

[21] Y.-J. Huang, Y. Huang, H. Baldassarre, B. Wang, A. Lazaris, M. Leduc, A. S. Bilodeau, A. Bellemare, M. Cote, P. Herskovits, Recombinant human butyrylcholinesterase from milk of transgenic animals to protect against organophosphate poisoning, Proc Natl Acad Sci USA, 104 (2007) 13603-13608.

[22] Y.-J. Huang, P. M. Lundy, A. Lazaris, Y. Huang, H. Baldassarre, B. Wang, C. Turcotte, M. Côté, A. Bellemare, A. S. Bilodeau, Substantially improved pharmacokinetics of recombinant human butyrylcholinesterase by fusion to human serum albumin, BMC biotechnology, 8 (2008) 50.

[23] F. Li, N. Vijayasankaran, A. Shen, R. Kiss, A. Amanullah, Cell culture processes for monoclonal antibody production, MAbs, Taylor & Francis, 2010, pp. 466-479.

[24] L. Xue, S. Hou, M. Tong, L. Fang, X. Chen, Z. Jin, H.-H. Tai, F. Zheng, C.-G. Zhan, Preparation and in vivo characterization of a cocaine hydrolase engineered from human butyrylcholinesterase for metabolizing cocaine, Biochem J, 453 (2013) 447-454.

[25] E. G. Duysen, C. F. Bartels, O. Lockridge, Wild-type and A328W mutant human butyrylcholinesterase tetramers expressed in Chinese hamster ovary cells have a 16-hour half-life in the circulation and protect mice from cocaine toxicity, Journal of Pharmacology and Experimental Therapeutics, 302 (2002) 751-758.

[26] 0. Lockridge, L. M. Schopfer, G. Winger, J. H. Woods, Large scale purification of butyrylcholinesterase from human plasma suitable for injection into monkeys; a potential new therapeutic for protection against cocaine and nerve agent toxicity, The journal of medical, chemical, biological, and radiological defense, 3 (2005) nihms5095.

[27] E. R. Lavallie, E. A. DiBlasio, S. Kovacic, K. L. Grant, P. F. Schendel, J. M. McCoy, A thioredoxin gene fusion expression system that circumvents inclusion body formation in the E. coli cytoplasm, Nature biotechnology, 11 (1993) 187-193.

[28] K.-M. Lo, Y. Sudo, J. Chen, Y. Li, Y. Lan, S.-M. Kong, L. Chen, Q. An, S. D. Gillies, High level expression and secretion of Fc-X fusion proteins in mammalian cells, Protein engineering, 11 (1998) 495-500.

[29] D. C. Roopenian, S. Akilesh, FcRn: the neonatal Fc receptor comes of age, Nature reviews immunology, 7 (2007) 715-725.

[30] W. Wang, J. Brady, K. Donato, M. Peshwa, K. Steger, Gram Scale Antibody Production Using CHO Cell Transient Gene Expression (TGE) via Flow Electroporation, J. Biomol. Screen, 20 (2015) 545-551.

[31] X. Chen, L. Xue, S. Hou, Z. Jin, T. Zhang, F. Zheng, C.-G. Zhan, Long-acting cocaine hydrolase for addiction therapy, Proc Natl Acad Sci USA, 113 (2016) 422-427.

[32] X. Chen, W. Cui, J. Deng, S. Hou, J. Zhang, X. Ding, X. Zheng, H. Wei, Z. Zhou, K. Kim, C.-G. Zhan, F. zheng, Development of Fc-fused Cocaine Hydrolase for Cocaine Addiction: Catalytic and Pharmacokinetic Properties, AAPS J, 20 (2018) 53. doi: 10.1208/s12248-12018-10214-12249.

[33] X. Chen, X. Huang, L. Geng, L. Xue, S. Hou, X. Zheng, S. Brimijoin, F. Zheng, C.-G. Zhan, Kinetic characterization of a cocaine hydrolase engineered from mouse butyrylcholinesterase, Biochemical Journal, 466 (2015) 243-251.

The invention claimed is:

1. A fusion polypeptide, comprising: an Fc polypeptide joined to an N- or C-terminal end of a butyrylcholinesterase (BChE) polypeptide, wherein (a) the Fc polypeptide is joined to the BChE polypeptide via a linker, the linker comprising a sequence selected from the sequences of SEQ ID NO: 2, SEQ ID NO: 4, SEQ ID NO: 19, and SEQ ID NO: 37;

(b) the Fc polypeptide has the sequence of SEQ ID NO: 8, or a fragment thereof, wherein the Fc polypeptide or fragment thereof includes 3 to 8 amino acid substitutions at 3 to 8 of residues selected from 1, 6, 12, 15, 24, 38, 40, 42, 58, 69, 80, 98, 101, 142, and 144; and (c) the fusion polypeptide has an improved production yield and biological half-life compared to a wild-type BChE polypeptide which is not fused.

2. The fusion polypeptide of claim 1, wherein the Fc polypeptide is a fragment wherein 1, 2, 3, 4, 5, 6, 7, 8, 9, 10, 11, 12, 13, 14, 15, or 16 amino acids are removed from the N-terminus of SEQ ID NO: 8.

3. The fusion polypeptide of claim 1, wherein the Fc polypeptide is selected from SEQ ID NO: 16, SEQ ID NO: 17, SEQ ID NO: 18, SEQ ID NO: 28, SEQ ID NO: 29, SEQ ID NO: 30, SEQ ID NO: 31, SEQ ID NO: 32, SEQ ID NO: 33, and SEQ ID NO: 34.

4. The fusion polypeptide of claim 1, wherein the BChE polypeptide has the sequence of SEQ ID NO: 10 or a fragment thereof, wherein the BChE polypeptide or fragment thereof includes 3 to 8 amino acid substitutions at 3 to 8 of residues chosen from 199, 227, 285, 286, 287, 328, 332, and 441.

5. The fusion polypeptide of claim 4, wherein the BChE polypeptide has a group of amino acid substitutions selected from A199S, F227A, F227S, F227Q, F227I, F227G, F227V, F227I, F227L, F227S, F227T, F227M, F227C, P285A, P285S, P285Q, P285I, P285G, P285M, P285N, P285E, S287G, A328W, Y332G, E441D, and combinations thereof.

6. The fusion polypeptide of claim 5, wherein the BChE polypeptide is a fragment wherein from 1 to 116 amino acids are removed from the N-terminus of SEQ ID NO: 10.

7. The fusion polypeptide of claim 5, wherein the BChE polypeptide is a fragment wherein from 1 to 432 amino acids are removed from the C-terminus of SEQ ID NO: 10.

8. The fusion polypeptide of claim 7, wherein the BChE polypeptide has a group of amino acid substitutions selected from A199S, F227A, F227S, F227Q, F227I, F227G, F227V, F227I, F227L, F227S, F227T, F227M, F227C, P285A, P285S, P285Q, P285I, P285G, P285M, P285N, P285E, S287G, A328W, Y332G, E441D, and combinations thereof.

9. The fusion polypeptide of claim 1, wherein the transient expression level of the polypeptide is at least 9 times higher than a reference BChE polypeptide that does not include the Fc polypeptide and linker.

10. The fusion polypeptide of claim 1 of SEQ ID NO: 35.

11. The fusion polypeptide of claim 1, wherein the BChE polypeptide is selected from: SEQ ID NO: 12, SEQ ID NO: 13, SEQ ID NO: 14, and SEQ ID NO: 15.

12. The fusion polypeptide of claim 11, wherein the Fc polypeptide is selected from SEQ ID NO: 16, SEQ ID NO: 17, and SEQ ID NO: 18.

13. The fusion polypeptide of claim 1, wherein the transient expression level of the polypeptide is about 9 times higher than a reference BChE polypeptide that does not include the Fc polypeptide and linker.

* * * * *